(12) United States Patent
Burn et al.

(10) Patent No.: US 7,906,902 B2
(45) Date of Patent: *Mar. 15, 2011

(54) METAL-CONTAINING DENDRIMERS

(75) Inventors: Paul Leslie Burn, St. Lucia (AU); Shih-Chun Lo, Oxford (GB); John Lupton, North Haugh (GB); Victor Christou, Oxford (GB); Jonathan N. G. Pillow, Cambridge (GB); Ifor David William Samuel, Fife (GB)

(73) Assignees: ISIS Innovation Limited, Oxford (GB); The University Court of the University of St. Andrews, Fife (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/564,908

(22) Filed: Sep. 22, 2009

(65) Prior Publication Data

US 2010/0072886 A1    Mar. 25, 2010

Related U.S. Application Data

(63) Continuation of application No. 10/468,716, filed as application No. PCT/GB02/00750 on Feb. 20, 2002, now Pat. No. 7,592,074.

(30) Foreign Application Priority Data

Feb. 20, 2001 (GB) .................................. 0104175.5
Mar. 14, 2001 (GB) .................................. 0106307.2

(51) Int. Cl.
*H01J 1/62* (2006.01)
*C09K 11/06* (2006.01)

(52) U.S. Cl. .... 313/504; 428/690; 428/917; 252/301.16

(58) Field of Classification Search .................. None
See application file for complete search history.

(56) References Cited

U.S. PATENT DOCUMENTS

| | | | |
|---|---|---|---|
| 5,041,516 A | 8/1991 | Frechet et al. | 528/44 |
| 5,150,006 A | 9/1992 | Van Slyke et al. | 313/504 |
| 5,432,014 A | 7/1995 | Sano et al. | 428/690 |
| 5,972,247 A | 10/1999 | Shi et al. | 252/583 |
| 6,083,634 A | 7/2000 | Shi | 428/690 |
| 6,558,818 B1 | 5/2003 | Samuel et al. | 428/690 |
| 6,632,543 B1 | 10/2003 | Kawamura et al. | 428/690 |
| 2002/0030647 A1 | 3/2002 | Hack et al. | 345/82 |
| 2002/0034656 A1 | 3/2002 | Thompson et al. | 428/446 |

(Continued)

FOREIGN PATENT DOCUMENTS

EP    1 009 041    6/2000

(Continued)

OTHER PUBLICATIONS

Adachi et al., "High-efficiency Organic Electrophosphorescent Devices with tris(2-phenylpryridine)iridium Doped into Electron-Transporting Materials," Appl. Phys. Lett., 77:904-906 (2000).

(Continued)

*Primary Examiner* — D. Lawrence Tarazano
*Assistant Examiner* — Camie S Thompson
(74) *Attorney, Agent, or Firm* — Marshall, Gerstein & Borun LLP

(57) ABSTRACT

This invention relates to a light emitting device which comprises at least one layer that contains an organometallic dendrimer having a core comprising a metal cation. The invention also relates to organometallic dendrimers and methods for producing the same.

46 Claims, 17 Drawing Sheets

*Fac* Tris[2-(Ar)Pyridine] Iridium (III) Complex

U.S. PATENT DOCUMENTS

| | | | |
|---|---|---|---|
| 2003/0165716 A1 | 9/2003 | Samuel et al. | 428/690 |
| 2004/0110029 A1 | 6/2004 | Burn et al. | 428/690 |
| 2004/0169463 A1 | 9/2004 | Burn et al. | 313/504 |
| 2005/0116622 A1 | 6/2005 | Lo et al. | 313/504 |
| 2005/0164029 A1 | 7/2005 | Burn et al. | 428/690 |

FOREIGN PATENT DOCUMENTS

| | | |
|---|---|---|
| EP | 1 009 042 | 6/2000 |
| EP | 1 009 043 | 6/2000 |
| EP | 1 009 044 | 6/2000 |
| JP | 1-105955 | 4/1989 |
| JP | 1-279240 | 11/1989 |
| JP | 8-012967 | 1/1996 |
| JP | 9-241265 | 9/1997 |
| WO | 99/21935 | 5/1999 |
| WO | 01/23344 | 4/2001 |
| WO | 01/59030 | 8/2001 |

OTHER PUBLICATIONS

Adronov et al., "Light-Harvesting Dendrimers," Chem. Commun. 1701-1710 (2000).

Armaroli et al., "A Copper(I) Bis-Phenanthroline Complex Buried in Fullerene-Functionalized Dendritic Black Boxes," Angew. Chem. Int. Ed. 38(24):3730-3733 (1999).

Baldo et al., "High-efficiency Fluorsecent Organic Light-Emitting Devices Using a Phosphorescent Sensitizer," Nature, 403:750-753 (2000).

Balzani et al., "Bottom-Up Strategy to Obtain Luminescent and Redox-Active metal Compleses of Nanometric Dimensions," Coord. Chem. Rev., 132:1-13 (1994).

Balzani et al., "Solar Energy Materials and Solar Cells," 38:159-173 (1995).

Beaupre et al., "Synthesis and Characterization of a Novel Polyester Derived from Substituted Terfluorene," Macromol. Rapid Commun. 21:1013-1018 (2000).

Bettenhausen et al., "Dendrimers With 1,3,4-Oxadiazole Units, 1," Macromol. Rapid Commun. 17: 623-631 (1996).

Bhyrappa et al., "Dendrimer-Metalloporphyrins: Synthesis and Catalysis," J. Am. Chem. Soc. 118: 5708-5711 (1996).

Burn et al., "Chemical Tuning of the Electronic Properties of Poly(p-phenylenevinylene)-Based Copolymers," J. Am. Chem. Soc. 115:10117-10124 (1993).

Chan et al., "Light-Emitting Multifunctional Rhenium (I) and Ruthenium (II) 2,2'-bipyridyl Complexes with Bipolar Character," Applied Physics Letters, 75(25):3920-3922 (1999).

Chen et al., "Recent Developments in Molecular Organic Electroluminescent Materials," Macromolecular Symposia, 125:1-48 (1998).

Deb et al., "A Simple Orthogonal Approach to Poly(phenylenevinylene) Dendrimers," J. Am. Chem. Soc., 119:9079-9080 (1997).

Devadoss et al., "Energy Transfer in Dendritic Macromolecules: Molecular Size Effects and the Role of an Energy Gradient," J. Am. Chem. Soc. 118:9635-9644 (1996).

Djurovich et al., "Ir(III) Cyclometalated Complexes as Efficient Phosphorescent Emiiters in Polymer Blend and Organic LEDs," Polymer Reprints, 41:770-771 (2000).

Fischer et al., "Dendrimers: From Design to Application—A Progress Report," Angew. Chem. Int. Ed. 38:884-905 (1999).

Freeman et al., "Dendrimer-Containing Light-Emitting Diodes: Toward Site-Isolation of Chromophores," J. Am. Chem. Soc. 122:12385-12386 (2000).

Gong et al., "Trifunctional Light-Emitting Molecules Based on Rhenium and Ruthenium Bipyridine Complexes," Adv. Mater., 10(16):1337-1340 (1998).

Gorman, "Metallodendrimers: Structural Diversity and Functional Behavior," Adv. Mater., 10(4):295-309 (1998).

Gutierrez et al., "Cyclometallation Palladium 2-Arylpyridine Complexes," J. Organomet. Chem., 202:341-350 (1980).

Halim et al., "Conjugated Dendrimers for Light-Emitting Diodes: Effect of Generation," Adv. Mater. 11(5):371-374 (1999).

Huang et al., "Design and Synthesis of Electroluminescent Europium Complexes Containing Dendron Substituted Diketone Ligands," Physical Organic, Photochemistry, Materials, Heterocycles, Aromatics, and Metal-Mediated Reactions Symposium (2000).

Issberner et al., "Dendrimers: From Generations and Functional Groups to Functions," Angew, Chem. Int. Ed. Engl., 33(23/24):2413-2420 (1994).

Jandke et al., "Phenylquinoxaline Polymers and Low Molar Mass Glasses as Electron-Transport Materials in Organic Light-Emitting Diodes," Macromolecules, 31:6434-6443 (1998).

Kawa et al., "Enhanced Luminescence of Lanthanide within Lanthanide-Cored Dendrimer Complexes," Thin Solid Films, 331(1-2):259-263 (1998).

Kelley et al., "The Synthesis of Bridged Oligophenylenes from Fluorene 1. Terphenyls and Quaterphenyls," J. Chem. Research (M), 2701-2709 (1997).

Kimura et al., "Energy Transfer within Ruthenium-Cored Rigid Metallodendrimers," Tetrahedron Letters, 41:6809-6813 (2000).

Kraft, "Self-Association of a 1,3,4-Oxadiazole-Containing Dendrimer," Chem. Commun., 77-79 (1996).

Kwok et al., "Synthesis and Light-Emitting Properties of Difunctional Dendritic Distyrylstilbenes," Macromolecules 2001.

Li et al., "Design, Synthesis, and Photodynamics of Light-Harvesting Arrays Comprised of a Porphyrin and One, Two, or Eight Boron-Dipyrrin Accessory Pigments," J. Am. Chem. 8oc. 120:10001-10017 (1998).

Lupton et al., "Control of Electrophosphorescence in Conjugated Dendrimer Light-Emitting Diodes," Adv. Funct. Mater., 11(4):287-294 (2001).

Miller et al., "Synthesis and Characterization of A Series of Monodisperse, 1,3,5-Phenylene-Based Hydrocarbon Dendrimers Including C276H186 and Their Fluorinated Analogues," J. Am. Chem. Soc. 114:1018-1025 (1992).

Murfee et al., "New Metallodendrimers Containing an Octakis(diphenylphosphino)-Functionalized Silsesquioxane Core and Ruthenium(III)-Based Chromophores," Inorg. Chem. 39:5209-5217 (2000).

Murfee et al., "New Starburst Metallodendrimers Based on Octa(Diphenylphosphino)-Functionalized Silsesquioxane Cores," Am. Chem. Soc. Div. Polym. Chem. 41(1):431-432 (2000).

Newkome et al., "Nanometric Dendritic Macromolecules: Stepwise Assembly by Double (2,2':6,2"-terpyridine)ruthenium(I) Connectivity," J. Mater. Chem. 7(7):1237-1244 (1997).

Nunez et al., "Dendritic Macromolecules for Light-Energy Conservation," Book of Abstracts, 215th ACS National Meeting, Dallas, Mar. 29-Apr. 2, 1998.

Palmans et al., Tensile Orientation Behavior of Alkoxy-Substituted Bis(phenylethynyl)benzene Derivatives in Polyolefin Blend Films,: Chem. Mater., 12:472-480 (2000).

Phelan et al., "Synthesis of Luminescent Materials Containing Rare Earth Cored Dendritic β-diketones," Sci-Mix Symposium (2001).

Pilow et al., "Synthetic Routes to Phenylene Vinylene Dendrimers," Synthetic Metals 102:1468-1469 (1999).

Plevoets et al., "Supramolecular Dendrimers with a [Ru(bpy)3]2+ Core and Naphthyl Peripheral Units," New J. Chem. 23(1):63-69 (1999).

Ranger et al., "New Well-Defined Poly(2,7-fluorene) Derivatives: Photoluminescence and Base Doping," Macromolecules, 30:7686-7691 (1997).

Sakamoto et al., "Synthesis, Characterization, and Electron-Transport Property of Perfluorinated Phenylene Dendrimers," J. Am. Chem. Soc. 122:1832-1833 (2000).

Serroni et al., "Polynuclear Metal Complexes of Nanometre Size. A Versatile Synthetic Strategy Leading to Luminescent and Redox-Active Dendrimers Made of an Osmium(II)-Based Core and Ruthenium(II)-Based Units in the Branches," J. Mater. Chem., 7(7):1227-1236 (1997).

Setayesh et al., "Polyfluorenes with Polyphenylene Dendron Side Chains: Toward Non-Aggregating, Light-Emitting Polymers," Journal of the American Chemical Society, 123:946-953 (2001).

Suslick et al., "Regioselective Epoxidations of Dienes with Manganese(III) Porphyrin Catalysts," J. Chem. Soc., Chem. Commun., 200-202 (1987).

van der Sluis et al., "Synthesis of Novel Phosphaalkene-Based Bidentate Ligands Mes*P=CH(3-R-Ar) (R=Pyridyl, Carbaldimino) and Formation of Three-Membered Palladacycles . . . by Carbapalladation of the P=C Double Bond," Organometallics, 18:1402-1407 (1999).

Venturi et al., "Electrochemical and Photochemical Properties of Metal-Containing Dendrimers," Topics in Current Chemistry, 197:193-228 (1998).

Vogtle et al., "Dendrimers with a Photoactive and Redox-Active [Ru(bpy)3]2+—Type Core: Photophysical Properties, Electrochemical Behavior, and Excited-State Electron-Transfer Reactions," J.Am. Chem. Soc. 121: 6290-6298 (1999).

Volz et al., "meso-Substituierte Porphyrine, 5[1] Korbporphyrine," Institut für Organische Chemie der Universitäat Karlsruhe, Z. Naturforsch., 43b:1043-1052 (1998).

Wang et al., "Electroluminescent Diodes from a Single-Component Emitting Layer of Dendritic Macromolecules," Advanced Materials, 8:193-241 (1996).

Wiesler et al., "Divergent Synthesis of Polyphenylene Dendrimers: The Role of Core and Branching Reagents Upon Size and Shape," Macromolecules 34:187-199 (2001).

Yang et al., "Use of Poly(9-vinylcarbazole) as Host Material for Iridium Complexes in High-efficiency Organic Light-emitting Devices," Jpn. J. Appl. Phys., 30:L828-L829 (2000).

Search Report in GB 0104175.5, dated Aug. 24, 2001.

International Search Report in PCT/GB02/00750, dated Jun. 17, 2002.

International Preliminary Examination Report in PCT/GB02/00750, dated Oct. 2, 2002.

A

B (a) AgOTf, 150°C, 28%

METAL-CONTAINING DENDRIMERS

CROSS-REFERENCE TO RELATED APPLICATIONS

This is a continuation of U.S. patent application Ser. No. 10/468,716 filed Feb. 13, 2004, (now U.S. Pat. No. 7,592,074) which is the U.S. national phase of International Application No. PCT/GB02/00750 filed Feb. 20, 2002, the entire disclosures of which are hereby incorporated by reference.

This invention relates to metal-containing dendrimers and light-emitting devices containing them.

A wide range of luminescent low molecular weight metal complexes are known and have been demonstrated as both light emitting and charge transporting materials in organic light emitting devices, in particular light emitting diodes (LEDs) also known as electroluminescent (EL) devices. Analysis of spin statistics associated with the injection of oppositely charged carriers which pair to form excitons shows that only 25% of the excitons formed in the LED are in the singlet state. Although it has been suggested that the barrier of 25% for singlet excitons may be exceeded under certain circumstances it is known to be far from 100%. For most organic materials only the singlet states can decay radiatively generating light, the triplet states decay non-radiatively. The possibility to extract luminescence from the triplet excited state has recently been demonstrated by inclusion of phosphorescent guest metallic complexes in host matrices. However, blend systems are sensitive to the concentration of the guest in the host and only low concentrations of the guest can be used before phase separation leads to aggregation and quenching.

In addition the metal complexes used to date have been designed to be volatile so that layers can be deposited by thermal evaporation. In many applications solution processing would be preferable to evaporation, but the current materials do not form good films when deposited by solution processing. In addition it would be advantageous to have guest host systems in which high levels of guest can be used. This is possible with dendritic materials.

According to the present invention these problems are solved by forming certain dendrimers with metal ions as part of the core. Dendrimers are highly branched macromolecules in which branched dendrons (a) so called dendrites) are attached to a core. The properties of the dendrimers make them ideal for solution processing and allow incorporation of metal complex chromophores, which have been demonstrated to be effective in light emitting devices (LEDs), into a solution processable system.

The known examples of metal containing dendrimers fall into three classes
(i) metal ion at the centre
(ii) metal ions on the periphery
(iii) metal ions at the branching points There is a range of metal containing dendrimers which have metal ions as part of the branching points and coordinating groups linking the metal ions, (see, e.g., Chem. Comm. (2000) 1701 and Adv. Mater. 10 (4) (1998) 295). The photoluminescent properties of some of these materials have been studied in solution, but the solid state luminescent properties have generally not been explored. It does not necessarily follow that a material that is luminescent in solution will also be luminescent in the solid state. Concentration quenching in the solid state is a common occurrence. In the dendrimers with metals ions at the branching points there is a high density of chromophores which makes concentration quenching particularly likely. Similarly in dendrimers with metal ions at the periphery, the metal ions in adjacent molecules will be close and again concentration quenching will be a problem.

The current invention is directed towards dendrimers with metal ions as part of the core. When the metal ion chromophore is sited at the core of the molecule, it will be relatively isolated from the core chromophores of adjacent molecules, which minimizes possible concentration quenching or triplet-triplet annihilation.

Further the organometallic dendrimers already disclosed generally do not have conjugated dendrons, and so are unlikely to work well in an electroluminescent device. For example the only lanthanide (Ln) dendrimers reported to date have a Ln core and benzyl ether Frechet-type dendrons. These compounds were shown to give PL emission, but have not been proven in EL devices. Kawa, M.; Frechet, J. M. J. Thin Solid Films, 331 (1998) 259]

Some organic dendrimers have been demonstrated to work in organic light emitting devices. However, the use of metal ion chromophores in the dendrimers opens up the range of materials that can be used, and may offer benefits in terms of stability and/or charge transport compared to organic systems. A particular benefit is the potential for highly efficient solution processed phosphorescent systems. Accordingly, the present invention provides a light emitting device which comprises a layer containing a metal ion containing dendrimer and, in particular, an organometallic dendrimer with a metal cation as part of its core, said core (or centre) not comprising a magnesium chelated porphyrin.

The present invention is particularly directed towards the use of dendrimers containing one or more at least partially conjugated organic dendrons with a metal ion as part of the core1. Such dendrimers form another aspect of the present invention. The atoms or groups coordinating/binding to the metal typically form part of the core itself e.g. fac-tris(2-phenylpyridyl)iridium III. Thus the dendrimers typically have the formula (I):

CORE-[DENDRITE]$_n$            (I)

in which CORE represents a metal ion or a group containing a metal ion, n represents an integer of 1 or more, each DENDRITE, which may be the same or different, represents an inherently at least partially conjugated dendritic structure comprising aryl and/or heteroaryl groups or nitrogen and, optionally, vinyl or acetylenyl groups connected via $sp^2$ or $sp$ hybridised carbon atoms of said (hetero)aryl vinyl and acetylenyl groups or via single bonds between N and (hetero)aryl groups, CORE terminating in the single bond which is connected to an $sp^2$ hybridised (ring) carbon atom of the first (hetero)aryl group or single bond to nitrogen to which more than one at least partly conjugated dendritic branch is attached, said ring carbon or nitrogen atom forming part of said DENDRITE. It is to be understood that the term "metal ion" or "metal cation", as used herein, describes the charge state the metal would have without any ligands attached (the oxidation state). In the dendrimers that contain a metal cation the overall charge of the dendrimer is neutral and the metal-ligand bonding will have more or less covalent character depending on the metal and ligand involved.

As used herein the term acetylenyl refers to acetylenyl groups that are di-valent, vinyl refers to vinyl groups that are di- or tri-valent, and aryl refers to aryl groups that are di-, tri- or multivalent. In a preferred embodiment the dendrites are conjugated.

The dendrimers of the invention are preferably luminescent in the solid state. The luminescent moiety may be partially or wholly within the core itself. The luminescence is preferably from the metal complex.

More preferably the organometallic dendrimer of the invention is phosphorescent in the solid state.

Suitable branching points include aryl and heteroaryl, which can be fused, aromatic ring systems and N. The links between branching points include bonding combinations such as aryl-aryl, aryl-vinyl-aryl, aryl-acetylenyl-aryl, aryl-aryl'-aryl (where aryl' may be different from aryl), N-aryl and N-aryl'-N. An individual dendron may contain one or more of each type of branching point. Moreover, in the case of the aryl-vinyl-aryl and aryl-acetylenyl-aryl linkages within the dendron there may be one or more aryl-vinyl or aryl-acetylenyl link between the branching points. Indeed there may be more than one vinyl or acetylenyl or aryl moiety between two aryl groups but preferably no more than three. Further, there can be advantages in using an asymmetric dendrimer i.e. where the dendrons are not all the same.

Thus the dendrimers may be ones having the formula (II):

CORE-[DENDRITE$^1$]$_n$[DENDRITE$^2$]$_m$ (II)

in which CORE represents a metal ion or a group containing a metal ion, n and m, which may be the same or different, each represent an integer of at least 1, each DENDRITE$^1$, which may be the same or different when n is greater than 1, and each DENDRITE$^2$, which may be the same or different when m is greater than 1, represent dendritic structures, at least one of said structures being fully conjugated and comprising aryl and/or heteroaryl groups or nitrogen and, optionally, vinyl and/or acetylenyl groups, connected via sp$^2$ or sp hybridized carbon atoms of said (hetero)aryl, vinyl and acetylenyl groups or via single bonds between N and (hetero)aryl groups, and the branching points and/or the links between the branching points in DENDRITE$^1$ being different from those in DENDRITE$^2$, CORE terminating in the single bond which is connected to a sp$^2$ hybridized (ring) carbon atom of the first (hetero)aryl group or single bond to nitrogen to which more than one conjugated dendritic branch is attached, said ring carbon atom or nitrogen forming part of said fully conjugated DENDRITE$^1$ or DENDRITE$^2$ and CORE terminating at the single bond to the first branching point for the other of said DENDRITE$^1$ or DENDRITE$^2$, at least one of the CORE, DENDRITE$^1$ and DENDRITE$^2$ being luminescent, as well as a light emitting dendrimer having the formula (III):

CORE-[DENDRITE]$_n$ (III)

in which CORE represents a metal ion or a group containing a metal ion, n represents an integer of 1 or more, each DENDRITE, which may be the same or different, represents an inherently at least partially conjugated dendritic molecular structure which comprises aryl and/or heteroaryl or N and, optionally, vinyl and/or acetylenyl groups connected via sp$^2$ or sp hybridized carbon atoms of said (hetero)aryl, vinyl and acetylenyl groups or via single bonds between N and (hetero)aryl groups, and wherein the links between adjacent branching points in said DENDRITE are not all the same, CORE terminating in the single bond which is connected to a sp$^2$ hybridized (ring) carbon atom of the first (hetero)aryl group or N to which more than one dendritic branch is attached, said ring carbon atom or N forming part of said DENDRITE, the CORE and/or DENDRITE being luminescent. In one aspect of the invention DENDRITE, DENDRITE$^1$ and/or DENDRITE$^2$ does not include N as a branching point and is conjugated.

It is to be understood that in formulae I, II and III CORE does not comprise a magnesium chelated porphyrin.

In this context, conjugated dendrons (dendrites) indicate that they are made up of alternating double and single bonds, apart from the surface groups. However this does not mean that the π system is fully delocalised. The delocalisationu of the π system is dependent on the regiochemistry of the attachments. In a conjugated dendron any branching nitrogen will be attached to 3 aryl groups.

Preferably in the organometallic dendrimer according to the invention the dendrimer has at least one inherently at least partially conjugated dendron. More preferably the dendrimer has at least two inherently at least partially conjugated dendrons. Most preferably all the dendrons are inherently at least partially conjugated.

The dendrimer may have more than one luminescent moiety. In a preferred embodiment the dendrimer incorporates at least two inherently luminescent moieties which moieties may or may not be conjugated with each other, wherein the dendron includes at least one of the said luminescent moieties. Preferably the luminescent moiety or moieties further from the core of the dendrimer have a larger HOMO-LUMO energy gap than the luminescent moiety or moieties closer to or partly or wholly within the core of the dendrimer. In another embodiment the HOMO-LUMO energy gap is substantially the same although the surface groups may change the HOMO-LUMO energy gap of the chromophores at the surface of the dendrite. Sometimes in, say, the second generation dendrimer the surface group makes the chromophore at the distal end of the dendrite of lower HOMO-LUMO energy compared to that of the next one in.

The relative HOMO-LUMO energy gaps of the moieties can be measured by methods known per se using a UV-visible spectrophotometer. One of the luminescent moieties may be, or be (partly or wholly) within, the core itself, which will thus preferably have a smaller inherent HOMO-LUMO gap energy than the other luminescent moiety or moieties in the dendron. Alternatively, or in addition, the dendrons themselves may each contain more than one luminescent moiety, in which case those further from the core will again preferably have larger inherent HOMO-LUMO gap energies than those closer to the core. In this case, the core itself need not be luminescent, although luminescent cores are generally preferred.

Preferably in an organometallic dendrimer according to the invention the HOMO-LUMO energy gap of the core is lower than that of the conjugated moieties in the dendrons.

Suitable surface groups for the dendrimers include branched and unbranched alkyl, especially t-butyl, branched and unbranched alkoxy, for example 2-ethylhexyloxy, hydroxy, alkylsilane, carboxy, carbalkoxy, and vinyl. A more comprehensive list includes a further-reactable alkene, (meth)acrylate, sulphur-containing, or silicon-containing group; a sulphonyl group; polyether group; a $C_1$-to-$C_{15}$ alkyl (preferably t-butyl) group; an amine group; a mono-, di- or tri-$C_1$-to-$C_{15}$ alkyl amine group; a —COOR group wherein R is hydrogen or $C_1$-to-$C_{15}$ alkyl; an —OR group wherein R is hydrogen, aryl, or $C_1$-to-$C_{15}$ alkyl or alkenyl; an —$O_2$SR group wherein R is $C_1$-to-$C_{15}$ alkyl or alkenyl; an —SR group wherein R is aryl, or $C_1$-to-$C_{15}$ alkyl or alkenyl; an —$SiR_3$ group wherein the R groups are the same or different and are hydrogen, $C_1$-to-$C_{15}$ alkyl or alkenyl, or an —SR' group (R' is aryl or $C_1$-to-$C_{15}$ alkyl or alkenyl), aryl, or heteroaryl. Typically t-butyl and alkoxy groups are used. Different surface groups may be present on different dendrons or different distal groups of a dendron. It is preferred that the dendrimer is solution processable i.e. the surface groups are such that the dendrimer can be dissolved in a solvent.

The surface group can be chosen such that the dendrimer can be photopatterned. For example a cross-linkable group is present which can be cross-linked upon irradiation or by chemical reaction. Alternatively the surface group comprises a protecting group which can be removed to leave a group which can be cross-linked. In general, the surface groups are selected so the dendrimers are soluble in solvents suitable for solution processing.

The aryl groups within the dendrons can be typically benzene, napthalene, biphenyl (in which case an aryl group is present in the link between adjacent branching points) anthracene, fluorene, pyridine, oxadiazole, triazole, triazine, thiophene and where appropriate substituted variations. These groups may optionally be substituted, typically by $C_1$ to $C_{15}$ alkyl or alkoxy groups. The aryl groups at the branching points are preferably benzene rings, preferably coupled at ring positions 1, 3 and 5, pyridyl or triazinyl rings. The dendrons themselves can contain a, or the, fluorescent chromophore.

It is possible to control the electron affinity of the dendrimers by the addition to the chromophores of electron-withdrawing groups, where appropriate, for example cyano and sulfone which are strongly electron-withdrawing and optically transparent in the spectral region we are interested in. Further details of this and other modifications of the dendrimers can be found in WO99/21935 to which reference should be made.

It will be appreciated that one or more of the dendrons attached to the core (provided that at least one dendron is a specified conjugated dendron) can be unconjugated. Typically such dendrons include ether-type aryl dendrons, for example where benzene rings are connected via a methyleneoxy link. It will also be appreciated that when there is more than one dendron, the dendrons can be of the same or different generation (generation level is determined by the number of sets of branching points). It may be advantageous for at least one dendron to be of the second, or higher, generation to provide the required solution processing properties.

The cores typically comprise a metal cation and attached ligands; the metal is typically central in the core and the core is typically luminescent. If it is not luminescent one or more of the dendrons should contain a luminescent group.

When the core comprises a metal cation and attached ligands it is typically a complex of a metal cation and one, two or more coordinating groups, at least one, and preferably at least two, of the coordinating groups being bound to a dendron. Typically the luminescence of the dendrimer will derive from that complex. When CORE in formula (I), (II) or (III) above represents a group containing a metal cation, CORE is typically a complex of a metal cation and two or more coordinating groups, at least one and preferably two or more of the said groups each being bound to a DENDRITE, DENDRITE$^1$ or DENDRITE$^2$ moiety as defined in formulae (I), (II) or (III), respectively, by the single bond in which CORE in these formulae terminates.

In one aspect of the invention CORE may be represented as a complex of the following formula (IV):

$$M[X—]_q Y_r \qquad (IV)$$

wherein M is a metal cation, each [X—], which are the same or different, is a coordinating group X attached to a single bond in which CORE terminates, each Y, which may be the same or different, is a coordinating group, q is an integer and r is 0 or an integer, the sum of (a.q)+(b.r) being equal to the number of coordination sites available on M, wherein a is the number of coordination sites on [X—] and b is the number of coordination sites on Y.

The single bond in the, or each, [X—] moiety, being a bond in which CORE terminates, connects to a dendron. Preferably there are at least two dendrons in a dendrimer, in which case q in formula (IV) is an integer of 2 or more. The said two or more dendrons typically have the structures represented by DENDRITE, DENDRITE$^1$ and/or DENDRITE$^2$ as defined in formulae (I) to (III) above. The coordinating groups Y, when present, are neutral or charged chelated ligands which are not attached to dendrons and which serve to fulfil the coordination requirements of the metal cation. Suitable metals include:

lanthanide metals: such as cerium, samarium, europium, terbium, dysprosium, thulium, erbium and neodymium, d-block metals, especially those in rows 2 and 3 i.e. elements 39 to 48 and 72 to 80: such as iridium, platinum, rhodium, osmium, ruthenium, rhenium, scandium, chromium, manganese, iron, cobalt, nickel and copper, and main group metals of the Periodic Table: such as metals from Groups IA, IIA, IIB, IIIB e.g. lithium, beryllium, magnesium, zinc, aluminum, gallium and indium. Suitable substituents Y, for rhenium in particular, include CO and halogen such as chlorine. For iridium dendrimers, the part of the ligands attached to the metal is preferably a nitrogen-containing heteroaryl, for example pyridine, attached to a (hetero) aryl where aryl can be a fused ring system, for example substituted or unsubstituted phenyl or benzothiophene. It should also be noted that the pyridine can also be substituted. Platinum dendrimers and especially platinum dendrimers with a porphyrin core with stilbene-based dendrons attached in the meso position are generally less preferred.

Preferably in an organometallic dendrimer according to the invention the metals as part of the core is not magnesium. Preferably in an organometallic dendrimer according to the invention the metal ions are exclusively at the centre.

It will be appreciated that the light emission can be either fluorescent or phosphorescent depending on the choice of metal and coordinating groups.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure colour emission useful for display applications. Due to the ability to harvest triplet excitons i.e. phosphorescence, the potential device efficiency can be higher than for fluorescent systems.

Main group metal complexes show ligand based, or charge transfer emission.

The emission colour is determined by the choice of ligand as well as the metal. A wide range of luminescent low molecular weight metal complexes are known and have been demonstrated in organic light emitting devices [see, e.g., Macromol. Sym. 125 (1997) 1-48, U.S. Pat. No. 5,150,006, U.S. Pat. No. 6,083,634 and U.S. Pat. No. 5,432,014]. Suitable ligands for di or trivalent metals are shown in FIG. 1; they include oxinoids (I) e.g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate (IA) and hydroxyquinoxalinol (IB), 10-hydroxybenzo[h]quinolinato (II), benzazoles (III), schiff bases (V), azoindoles (IV), chromone derivatives (VI), 3-hydroxyflavone (VII), and carboxylic acids such as salicylato (VIII) amino carboxylates (IX) and ester carboxylates (X). The substituents including the R and X groups are typically halogen, alkyl, alkoxy, haloalkyl, cyano, amino, amido, sulfonyl, carbonyl, aryl or heteroaryl on the (hetero)aromatic rings which may modify the emission colour. The R groups in formulae V and X are typically alkyl or aryl. The alkyl groups are typically alkyl groups of 1 to 6 carbon atoms, especially 1 to 4 carbon atoms such as methyl, ethyl, propyl and butyl. The aryl groups are typically phenyl groups.

The d-block metals form organometallic complexes with carbon or nitrogen donors such as porphyrin, 2-phenyl-pyridine, 2-thienylpyridine, benzo[h]quinoline, 2-phenylbenzoxazole, 2-phenylbenzothiazole or 2-pyridylthianaphthene and iminobenzenes. The (hetero)aromatic rings can be substituted for example as for the R and X groups given above. The emission of d-block complexes can be either ligand based or due to charge transfer. For the heavy d-block elements, strong spin-orbit coupling allows rapid intersystem crossing and emission from triplet states (phosphorescence).

In fluorescent electroluminescent devices, many excitons form in the non-emissive triplet state, reducing the efficiency of light emission.

Hence devices based on phosphorescent emitters, which can harvest the triplet excitons, have the potential for much higher efficiency than devices based on fluorescent emitters.

The dendrimers can be built in a convergent or divergent route, but a convergent route is preferred. Thus the dendrons are attached to the appropriate ligands and these are subsequently attached to the metal cation to form the dendritic metal complex. Optionally other non-dendritic ligands can subsequently be attached to said complex. Alternatively a ligand with a suitably reactive functional group can be complexed to the metal ion, and then reacted with appropriately functionalised dendrons. In this latter method, not all ligands have to have the reactive functional groups, and thus this method allows the attachment of dendrons to some but not all of the ligands complexed to the metal. A key property of the dendrons is to impart solution processibility to the metal complex and therefore allow the formation of good quality thin films suitable for use in light-emitting diodes.

The dendritic metal complexes may be homoleptic or contain more than one type of dendritic ligand, as discussed above. Alternatively, the metal complex may contain one or preferably more than one, e.g. 2 or 3, dendritic ligands plus one or more non-dendritic ligands. For example, with terbium complexes it is possible to have three dendritic ligands terminating in a carboxylate moiety for complexing to the metal plus one or more coligands to satisfy the co-ordination sphere of the metal cation. Suitable neutral co-ligands include 1,10-phenanthroline, bathophenanthroline, 2,2'-bipyridyl, benzophenones, pyridine N-oxide and derivatives of these. Also for iridium it is possible to have two dendritic phenylpyridine ligands with the third ligand a non-dendritic phenylpyridine ligand. It is desirable that the number of dendritic ligands is sufficient to provide the required solution processing. In the case of the dendritic metal complexes where all the ligands are different the method of preparation may give rise to a statistical mixture of all complex types. This is not necessarily disadvantageous providing that the optical, electronic, and processing properties are satisfactory. In the case of mixed dendron complexes it is preferable that the moieties forming the attachment point to metal are all the same or have similar binding constants. In the case of dendritic complexes that contain two or more different dendrons at least one should desirably be a conjugated dendron. The conjugated dendrons can be comprised of a number of different types of branching points.

The surface groups and dendrites can be varied so the dendrimers are soluble in solvents, such as toluene, THF, water and alcoholic solvents such as methanol, suitable for the solution processing technique of choice. Typically t-butyl and alkoxy groups have been used. In addition, the choice of dendron and/or surface group can allow the formation of blends with dendrimers (organic or organometallic), polymer or molecular compounds. In one embodiment of the present invention there is a blend of a phosphorescent dendrimer possessing an organometallic core and a dendrimer which possesses the same dendron type but a different core.

According to another aspect of the present invention the organometallic dendrimer can be incorporated into a light emitting device as either a homogeneous layer or as a blend with another dendrimer (organic or organometallic), polymer or molecular compound. In one embodiment we show the first example that we are aware of a d-block phosphorescent material being used as a homogenous light emitting layer in an LED. We have also found that when a phosphorescent organometallic dendrimer is blended with a fluorescent host the emission spectrum may depend on the driving frequency of electrical pulsing. A device can be driven by applying voltage (or current) pulses with a certain duration and period (together describing the driving frequency). Within the regime where the duration and/or period of the pulses are on a timescale of a similar order of magnitude to the phosphorescence decay lifetime then the emission spectrum may be sensitive to the driving frequency. In another embodiment, it has been found that it is advantageous to blend the dendrimer with a charge transporting material. In particular it has been found that the presence of a hole-transporting and/or a bipolar material and/or electron transporting material is advantageous. In a further embodiment the bipolar material should contain carbazole units. Another embodiment has one or more of each type of charge transporting material.

In one embodiment the device according to the invention comprises the dendrimer in the light emitting layer, preferably the dendrimer is the light emitting material. In a device according to the invention the dendrimer is preferably fluorescent in the solid state. In a device according to the invention the dendrimer is preferably phosphorescent in the solid state.

In a further embodiment in a device according to the invention the dendrimer is blended with at least one other dendrimer and/or polymer and/or molecular material. Preferably the organometallic dendrimer is phosphorescent in the solid state and is blended with a corresponding non-metallic dendrimer which possesses the same dendritic structure as that of the organometallic dendrimer, more preferably the molar ratio of organometallic dendrimer to other component is from 1: to 1:100. The device according to the invention may comprise, in addition to the light emitting layer, at least one charge transporting and/or injection layer. A further embodiment of the invention comprises a blend of an organometallic dendrimer according to the invention and a corresponding non-metallic dendrimer having the same dendritic structure as that of the organometallic dendrimer, preferably the molar ratio or organometallic dendrimer to non-organometallic dendrimer is from 1:1 to 1:100

In a further embodiment in a device according to the invention the color of the emission is controlled by the duration and frequency of the driving electrical pulse.

The organometallic dendrimers can be incorporated into an LED in a conventional manner. In its simplest form, an organic light emitting or electroluminescent device can be formed from a light emitting layer sandwiched between two electrodes, at least one of which must be transparent to the emitted light. Such a device can have a conventional arrangement comprising a transparent substrate layer, a transparent electrode layer, a light emitting layer and a back electrode. For this purpose the standard materials can be used. Thus, typically, the transparent substrate layer is typically made of glass although other transparent materials such as PET, can be used.

The anode, which is generally transparent, is preferably made from indium tin oxide (ITO) although other similar materials including indium oxide/tin oxide, tin oxide/antimony, zinc oxide/aluminum, gold and platinum can also be used. Conducting polymers such as PANI (polyaniline) or PEDOT can also be used.

The cathode is normally made of a low work function metal or alloy such as Al, Ca, Mg, Li, or MgAl or optionally with an additional layer of LiF. As is well known, other layers may also be present, including a hole transporting material and/or an electron transporting material. When the dendrimer is a phosphorescent emitter, it has been found that it is particularly beneficial to have a hole-blocking/electron-transporting layer between the light emitting dendrimer layer and the cathode. In an alternative configuration, the substrate may be an opaque material such as silicon and the light is emitted through the opposing electrode.

An advantage of the present invention is that the layer containing the dendrimer can be deposited from solution. Conventional solution processing techniques such as spin coating, printing, and dip-coating can be used to deposit the dendrimer layer. In a typical device a solution containing the dendrimer is applied over the transparent electrode layer, the solvent evaporated, and then subsequent layers applied. The film thickness is typically 10 nm to 1000 nm, preferably less than 200 nm, more preferably 30-120 nm.

The invention will be described in the Examples which follow, with reference to the accompanying drawings wherein.

REFERENCE EXAMPLE 1

G0-Br (R1)

4-(2'-Ethylhexyloxy)phenylbromide

Figure 1:
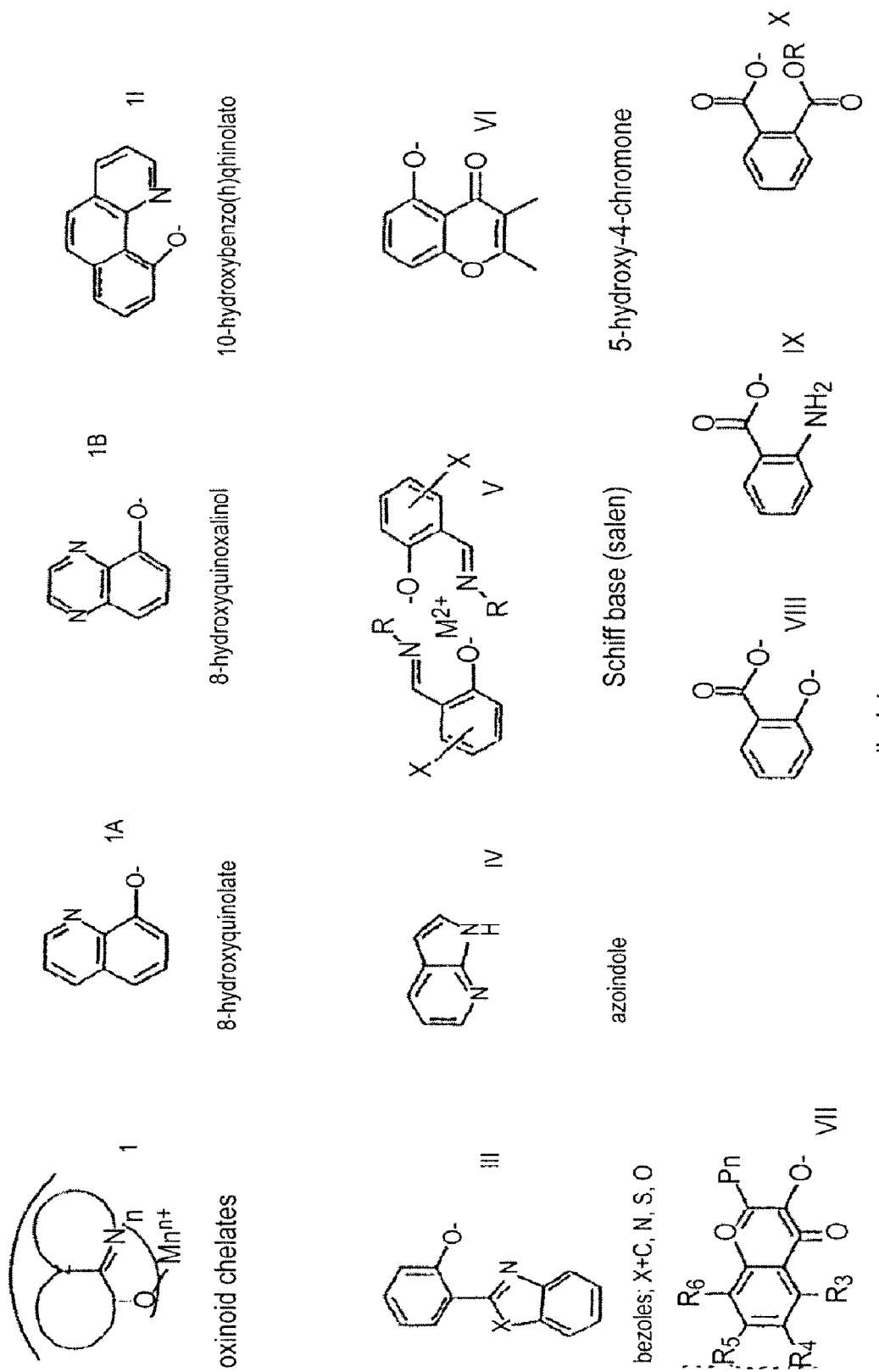
FIG. 1 shows coordinating groups for di- or tri-valent metals.
Figure 2:
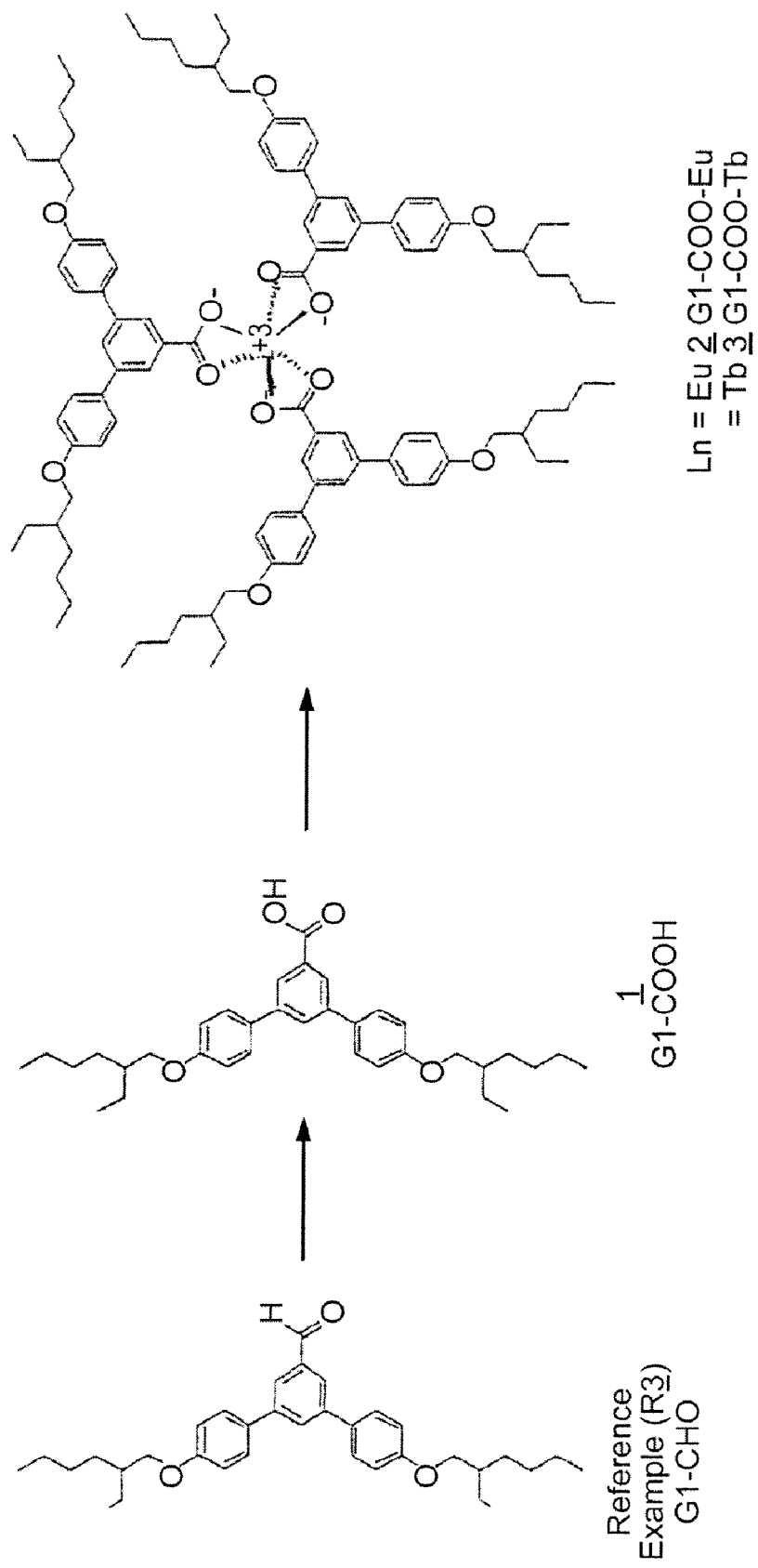
FIG. 2 shows the structure of first generation lanthanide dendrimers.
Figure 3:
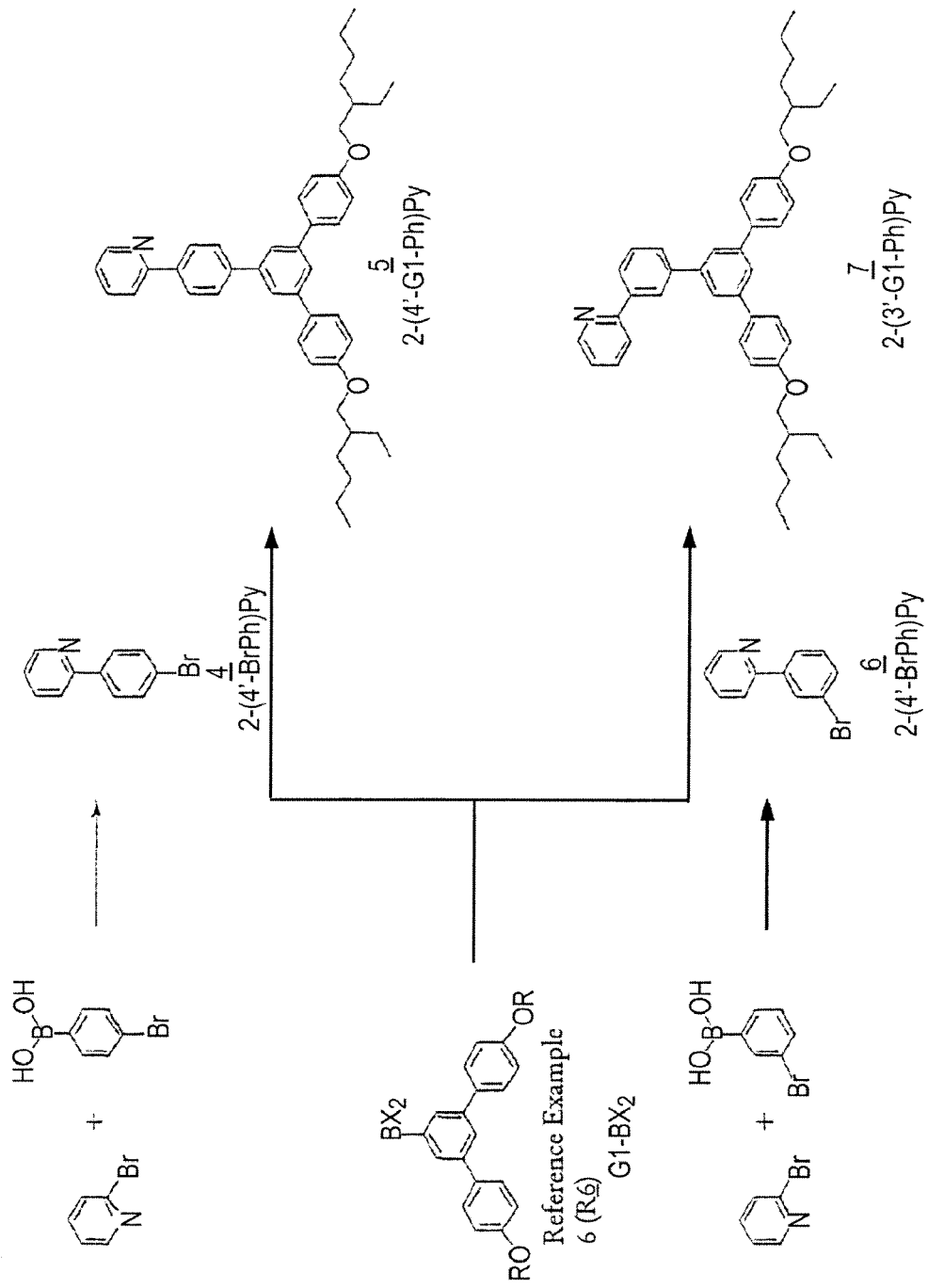
FIG. 3 shows a reaction scheme for synthesis of first generation 1-arylpyridine ligands.
Figure 4:
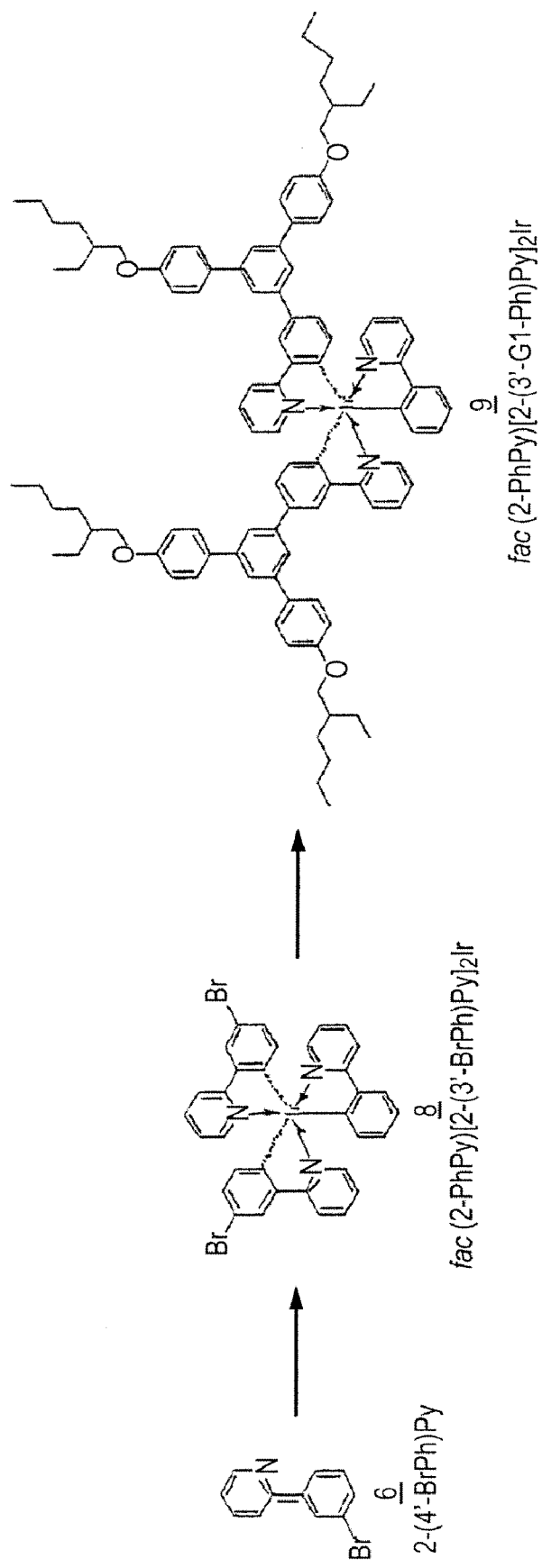
FIG. 4 shows a reaction scheme for synthesis of tris[2-(Ar)pyridine]iridium (III) complex.
Figure 5:
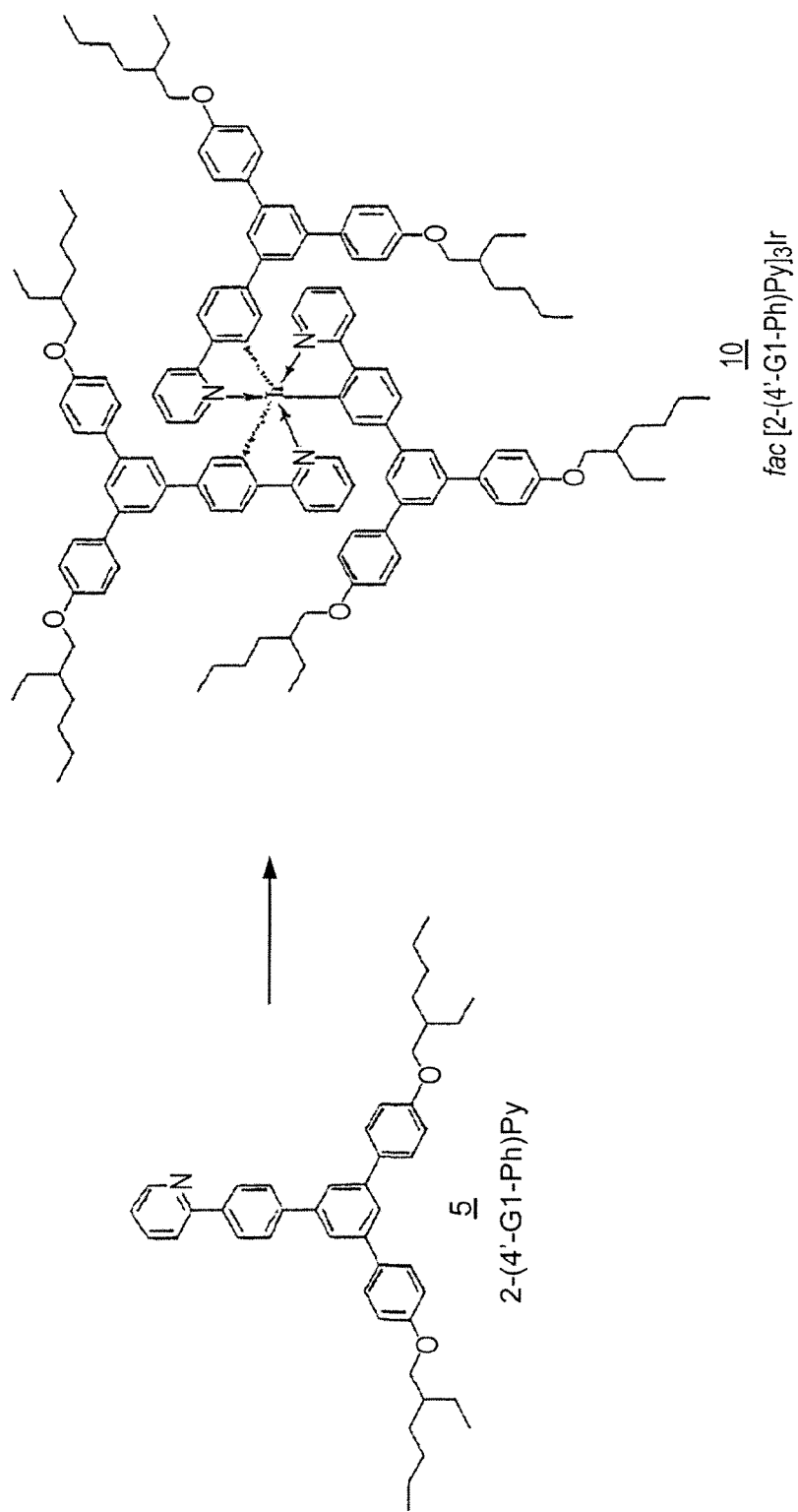
FIG. 5 shows the structure of Fac tris[2-(4'-G1-phenyl)pyridine]iridium (III) complex.

Sodium hydride (60% dispersion in oil, 17.4 g, 435 mmol) was added in portions to a cold (ice-bath) solution of 4-bromophenol (49.0 g, 283 mmol) in dry DMF (780 cm$^3$). The mixture was stirred at that temperature for 2 h and the ice bath was removed. A solution of 2-ethylhexylbromide (54.4 cm$^3$, 306 mmol) in 150 cm$^3$ of dry DMF was added dropwise through an addition funnel to the reaction mixture and the reaction was stirred at room temperature overnight (21 h). The resultant mixture was diluted with water (400 cm$^3$) and ether (500 cm$^3$). The two phases were separated. The aqueous layer was extracted with ether (3×300 cm$^3$) and the organic portion and the ether extracts were dried over anhydrous MgSO$_4$, filtered and the filtrate was collected and evaporated under reduced pressure to leave yellow oil. Column chromatography over silica gel (half amount each time) with light petroleum as eluent afforded R1 (54.1 g, 67%) as colourless oil; $\lambda_{max}$(CH$_2$Cl$_2$)/nm 284 ($\epsilon$/dm$^3$mol$^{-1}$cm$^{-1}$ 1251), and 291 sh (1001); $\delta_H$(400 MHz; CDCl$_3$) 0.83-0.97 (6H, m, Me), 1.30-1.57 (8H, m, CH$_2$), 1.68-1.79 (1H, m, CH), 3.78-3.84 (2H, m, ArOCH$_2$), 6.74-6.80 (2H, m, ArH), and 7.33-7.40 (2H, m, ArH); $\delta_C$(100 MHz; CDCl$_3$) 11.1, 14.1, 23.0, 23.8, 29.1, 30.4, 39.3, 70.7, 112.4, 116.3, 132.1, and 158.5.

REFERENCE EXAMPLE 2

G0-SnBu$_3$ (R2)

1-(2'-Ethylhexyloxy)-4-(tri-n-butyl)stannylbenzene

Tert-butyl lithium (1.7 M, 21.7 cm$^3$, 36.8 mmol) was added slowly over 10 min to a cold (dry-ice/acetone bath) solution of G0-Br R1 (7.00 g, 24.5 mmol) in 54 cm$^3$ of ether under argon atmosphere. The mixture was stirred at −78° C. for 2 h and tri-n-butyl tin chloride (10 cm$^3$, 36.8 mmol) was added dropwise over 5 min to the mixture, which was stirred at −78° C. for 1 h before being removed from the dry-ice/acetone bath. The mixture was stirred at room temperature for a further 3 h before being quenched with 10% of NH$_4$Cl$_{(aq)}$ (20 cm$^3$). The aqueous layer was separated and extracted with DCM (2×10 cm$^3$). The dichloromethane (DCM) extracts and the ether portion were then dried (MgSO$_4$) and filtered. The solvents were removed completely. Kugolrohr distillation removed the excess tri-n-butyl tin chloride to leave 12.0 g (99%) of R2 as a light yellow oil; $\lambda_{max}$(CH$_2$Cl$_2$)/nm 277 ($\epsilon$/dm$^3$mol$^{-1}$cm$^{-1}$ 826), and 284 sh (660); $\delta_H$(200 MHz; CDCl$_3$) 0.81-1.09 (15H, m, Me), 1.21-1.81 (27H, m, CH$_2$ & CH), 3.84 (2H, ArOCH$_2$), 6.91 (2H, m, ArH), and 7.36 (2H, ArH).

REFERENCE EXAMPLE 3

G1-CHO(R3)

3,5-Di[4'-(2"-ethylhexyloxy)phenyl]benzaldehyde

Method 1:

A mixture of R2 (8.50 g, 17.2 mmol), 3,5-di-bromobenzaldehyde (1.18 g, 4.47 mmol), CuI (790 mg, 4.15 mmol), tetrakis(triphenylphosphine)palladium (0) (790 mg, 0.684 mmol) and 20 cm$^3$ of distilled triethylamine was heated at reflux for 14 h under argon. The reaction mixture was allowed to cool and then filtered through a plug of silica gel using DCM as eluent. The filtrate was collected and the solvent was completely removed to yield a brown yellow oil. The residue was purified by column chromatography over silica using ethyl acetate-light petroleum (0:1 to 1:10) as eluent to give R3 as a colourless oil (1.91 g, 83%); $v_{max}$/cm$^{-1}$ (neat) 1700 (C=O); $\lambda_{max}$(CH$_2$Cl$_2$)/nm 247 ($\epsilon$/dm$^3$mol$^{-1}$cm$^{-1}$ 22406), 274 (27554), and 339 sh (1817); $\delta_H$(400 MHz; CDCl$_3$) 0.88-1.01 (12H, m, Me), 1.30-1.61 (16H, m, CH$_2$), 1.73-1.84 (2H, m, CH), 3.94 (4H, m, ArOCH$_2$), 7.04 (4H, m, ArH), 7.62 (4H, m, ArH), 7.99 (3H, s, ArH), and 10.13 (1H, s, CHO); $\delta_C$(100 MHz; CDCl$_3$) 11.1, 14.1, 23.1, 23.9, 29.1, 30.5, 39.4, 70.6, 115.0, 126.0, 128.2, 130.8, 131.9, 137.4, 142.3, 159.6, and 192.5; m/z [CI(NH$_3$)] 533 (MNH$_4^+$), and 515 (M$^+$).

Method 2:

A mixture of 4B (213 mg, 0.851 mmol), 3,5-di-bromobenzaldehyde (98 mg, 0.370 mmol), tetrakis(triphenylphosphine)palladium (0) (30 mg, 0.026 mmol), 2 M Na$_2$CO$_{3(aq)}$ (0.5 cm$^3$), EtOH (0.5 cm$^3$) and toluene (1.1 cm$^3$) was degassed and heated at reflux (with bath temperature of 96° C.) under argon for 18 h. The mixture was allowed to cool. Water (4 cm$^3$) and ether (5 cm$^3$) were added to the mixture. The two phases were separated. The aqueous layer was extracted with ether (3×5 cm$^3$). The organic layer and the ether extracts were combined and dried over anhydrous magnesium sulfate and filtered. The solvents were completely removed. The residue was purified by column chromatography over silica gel using light petroleum (60-80° C.) as eluent to give 172 mg (90%) of R3 as a colourless oil.

REFERENCE EXAMPLE 4

G0-B(X)$_2$ 4-(2'-Ethylhexyloxy)phenylboronic acid

Tert-butyl lithium (1.7 M, 66.0 cm$^3$, 112 mmol) was added carefully to a cold (dry-ice/acetone bath) solution of G0-Br R1 (20.0 g, 70.1 mmol) in 300 cm$^3$ of anhydrous THF under an argon atmosphere. The mixture was stirred at −78° C. for 1 h and then tri-methyl borate (57.2 cm$^3$, 421 mmol) was added slowly to the cold mixture. The reaction was stirred at −78° C. for 2 h before being removed from the dry-ice/acetone bath. The mixture was then stirred at room temperature for further 2.5 h before being quenched with 3 M HCl$_{(aq)}$ (30 cm$^3$). The two layers were separated. The aqueous layer was extracted with DCM (3×30 cm$^3$). The organic layer and the DCM extracts were combined and dried over anhydrous magnesium sulfate, filtered and the solvents were completely removed. Purification by column chromatography over silica gel using ethyl acetate-light petroleum (1:10), and then ethyl acetate-DCM (0:1 to 1:3) as eluent gave two major bands; less polar compound 4A, 6.44 g as a colourless oil; $\delta_H$(200 MHz; CDCl$_3$) 0.81-1.05 (6H, m, Me), 1.22-1.62 (8H, m, CH$_2$), 1.68-1.88 (1H, CH), 3.91 (2H, m, ArOCH$_2$), 6.98 (2H, m, ArH), and 7.77 (2H, m, ArH); and more polar compound 1 a trimer 4B, 8.40 g as a colourless oil; $\delta_H$(200 MHz; CDCl$_3$) 0.85-1.07 (6H, m, Me), 1.30-1.64 (8H, m, CH$_2$), 1.70-1.90 (1H, m, CH), 3.95 (2H, ArOCH$_2$), 7.03 (2H, ArH), and 8.18 (2H, m, ArH).

Note: either compound 4A or 4B can be used in the reaction to form the next generation dendrons. In either case of 4A or 4B being a dimer the number of protons in the $^1$H NMR should be considered as a ratio.

REFERENCE EXAMPLE 5

G1-Br (R5)

3,5-Di[4'-(2"-ethylhexyloxy)phenyl]phenyl bromide

A mixture of the boronic acid 4B (7.90 g, 31.6 mmol), 1,3,5-tribromobenzene (4.53 g, 14.4 mmol), tetrakis(triphenylphosphine)palladium (0) (1.16 g, 1.00 mmol), 2 M Na$_2$CO$_{3(aq)}$ (15 cm$^3$), EtOH (15 cm$^3$) and toluene (43 cm$^3$) was degassed and heated at reflux (with bath temperature of 101° C.) under argon for 22 h. The mixture was allowed to cool. Water (20 cm$^3$) and ether (30 cm$^3$) were added to the mixture. The two phases were separated. The aqueous layer was extracted with ether (3×20 cm$^3$). The organic layer and the ether extracts were combined and dried over anhydrous magnesium sulfate and filtered. The solvents were completely removed. The residue was purified by column chromatography over silica gel using light petroleum (60-80° C.) as eluent to give 6.04 g (74%) of R5 as a colourless oil; $\delta_H$(200 MHz; CDCl$_3$) 0.82-1.02 (12H, m, Me), 1.26-1.60 (16H, m, CH$_2$), 1.70-1.83 (2H, m, 2×CH), 3.90 (4H, m, ArOCH$_2$), 6.99 (4H, m, ArH), 7.54 (4H, m, ArH), and 7.62 (3H, s, ArH); m/z [MALDI] 566 (M$^+$). In addition, 910 mg (9%) of the tris-substituted compound as a colourless oil was isolated; $\delta_H$(200 MHz; CDCl$_3$) 0.82-1.02 (18H, m, Me), 1.25-1.63 (24H, m, CH$_2$), 1.70-1.83 (3H, m, CH), 3.90 (6H, m, ArOCH$_2$), 7.01 (6H, m, ArH), 7.62 (6H, m, ArH), and 7.65 (3H, s, ArH); m/z [APCI$^+$] 692 (MH$^+$).

REFERENCE EXAMPLE 6

G1-BX$_2$ (R6)

Tert-butyl lithium (1.7 M, 3.0 cm$^3$, 5.15 mmol) was added to a cold (dry-ice/acetone bath) solution of aryl bromide R5 (1.82 g, 3.22 mmol) in 18 cm$^3$ of anhydrous THF under argon atmosphere. The reaction mixture, changing to a deep reddish brown was stirred at −78° C. for 1 h. Tri-n-butyl borate (5.2 cm$^3$, 19.3 mmol) was added slowly to the mixture and the reaction was stirred at −78° C. for 1 h before being removed from the dry-ice/acetone bath. The mixture was then stirred at room temperature for further 3.5 h before being quenched with 3 M HCl$_{(aq)}$ (7 cm$^3$). The two layers were separated. The aqueous layer was extracted with DCM (3×5 cm$^3$). The organic layer and the DCM extracts were dried over anhydrous magnesium sulfate and filtered. The solvents were completely removed. Purification on silica gel column using ethyl acetate-light petroleum (1:10), and then ethyl acetate-DCM (1:4) as eluent gave 1.63 g (96%) of R6 as a colourless oil. The structure of R6 has not been fully determined however can be used to form higher generation dendrons in excellent yield.

REFERENCE EXAMPLE 7

Figure 9:
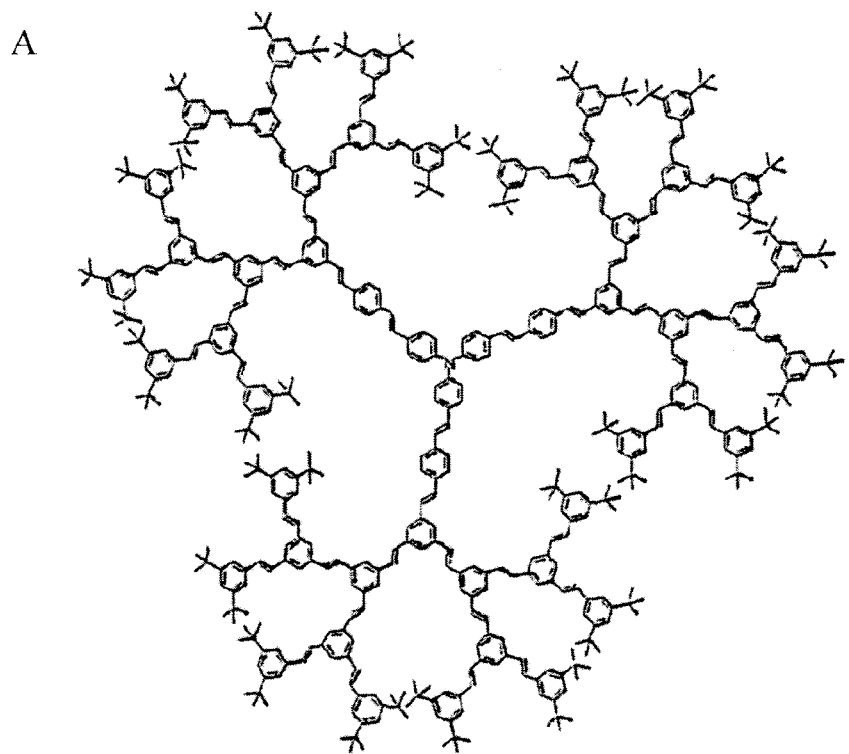
FIG. 9 shows structures of Dendrimer A and Dendrimer B.
Figure 9:
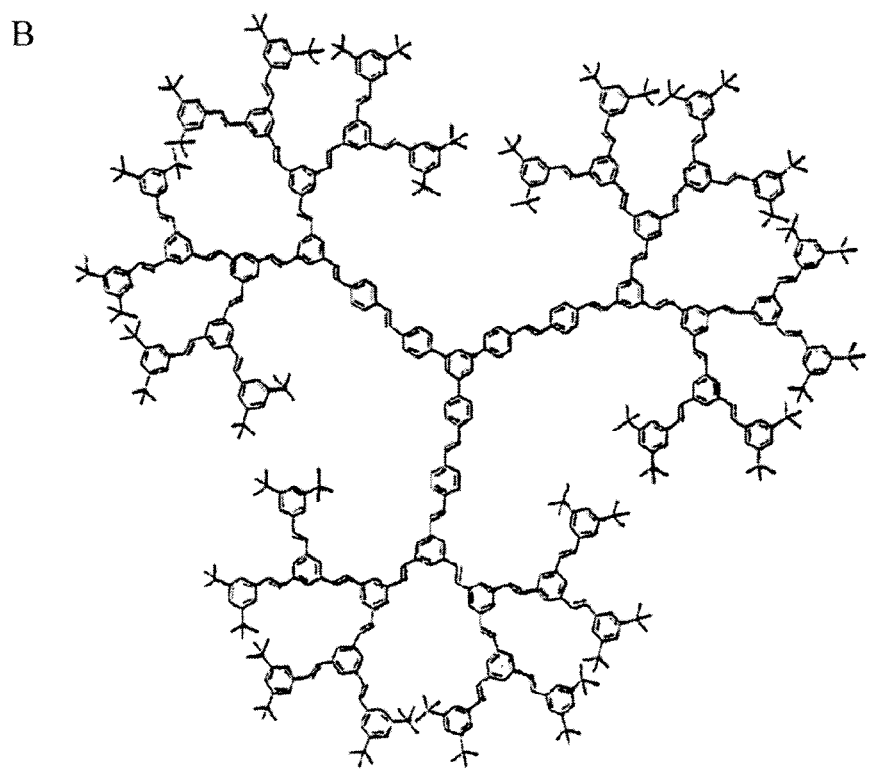

[G-3]$_3$N (Compound A in FIG. 9)

Potassium tert-butoxide (122 mg, 1.09 mmol) was added to a solution of [G-3]-Phosphonate Reference Example 7A (55 mg, 0.218 mmol) and Reference Example 8 (34.6 mg, 0.054 mmol) in dry tetrahydrofuran (15 mL) and heated at reflux for approximately 21.5 h under argon and then the solvent was removed. Dichloromethane (50 mL) was added and the organic layer was washed with water (50 mL) and brine (50 mL), dried over anhydrous sodium sulfate, filtered, and the solvent removed to leave a yellow solid. The residue was difficult to purify by column chromatography over silica. When a dichloromethane/light petroleum mixture (1.5:3.5 to 2:3) was used as eluent a small amount of pure material could be isolated (≈90 mg). The remaining impure material (≈260 mg) and iodine (17 mg, 0.07 mmol) were dissolved in toluene (6 ml) and heated at reflux for 5.2 h. The solvent was removed and the residue purified by column chromatography over silica using a dichloromethane/light petroleum mixture (1.5:3.5 to 2:3) as eluent. The main fraction was collected and the solvent removed. The residue was combined with the first fraction of pure material to give 21 (268 mg, 63%), mp 266-267° C.

Anal. Calcd for $C_{594}H_{687}N$: C, 91.0; H, 8.8; N, 0.2. Found: 90.6; H, 9.3; N, nil. $\nu_{max}$(KBr disk)/cm$^{-1}$: 958 (C=C—H trans). $\lambda_{max}$(CH$_2$Cl$_2$)/nm: 239 (log $\epsilon$/dm$^3$mol$^{-1}$cm$^{-1}$ 5.52), 323 (6.08), 334 sh (6.04) and 424 (5.16). $\delta_H$(400 MHz; CDCl$_3$): 1.40 (432H, s, t-Bu), 7.03-7.37 (96H, cv H, G-1 vinyl H, G-2 vinyl H and G-3 vinyl H), 7.17 and 7.50 (12H, AA'BB', cp H), 7.39 (24H, dd, J=1.5, sp H), 7.45 (48H, d, J=1.5, sp H), 7.59 and 7.63 (12H, AA'BB', cp H), 7.65-7.77 (63H, by H). m/z (MALDI): 7839.4 (M$^+$, 100%). GPC: $\overline{M}_w$=1.0×10$^4$ and $\overline{M}_n$=8.8×10$^3$.

EXAMPLE 1

G1-COOH (1)

3,5-Di[4'-(2"-ethylhexyloxy)phenyl]benzoic acid

Dichloromethane (DCM) (0.8 cm$^3$), a solution of the aldehyde of Reference Example 3(3,5-di[4'-(2"-ethylhexyloxy)phenyl]benzaldehyde) (515 mg, 1.00 mmol) in 5 cm$^3$ of DCM and tetra-n-butylammonium bromide (64 mg, 0.200 mmol) were added sequentially to a cold (ice-bath) mixture of KMnO$_4$ (474 mg, 3.00 mmol), NaOH (20 mg, 0.500 mmol) and 0.8 cm$^3$ of water. The mixture was then stirred at 0-2° C. for 30 min and then at room temperature for another 16 h before being quenched with acetic acid (31 drops). The mixture was passed through a small plug of celite with DCM and then ethyl acetate as eluents. The filtrate was collected and the solvents were completely removed. The crude residue was purified by column chromatography over silica gel with ethyl acetate-DCM-acetic acid (0:1:0 to 1:4:0.01) as eluent to give 458 mg (86%) of 1 as a yellowish solid; mp 105° C.; (Found: C, 79.2; H, 8.7. $C_{35}H_{46}O_4$ requires C, 79.2; H, 8.7%); $\nu_{max}$/cm$^{-1}$ (neat) 1687 (C=O); $\lambda_{max}$(CH$_2$Cl$_2$)/nm 231 ($\epsilon$/dm$^3$mol$^{-1}$cm$^1$ 27864), 271 (42017), and 327 (3096); $\delta_H$(400 MHz; CDCl$_3$) 0.90-1.03 (12H, m, Me), 1.35-1.63 (16H, m, CH$_2$), 1.77-1.86 (2H, m, CH), 3.93 (4H, m, ArOCH$_2$), 7.04 (4H, m, ArH), 7.63 (4H, m, ArH), 7.98 (1H, s, ArH), and 8.27 (2H, hr s, ArH), (COOH not observed); $\delta_C$(100 MHz; CDCl$_3$) 11.1, 14.1, 23.1, 23.9, 29.1, 30.5, 39.4, 70.6, 93.2, 114.9, 126.6, 128.2, 130.3, 132.2, 141.8, 159.4, and 185.6; m/z [CI(NH$_3$)] 549 (MNH$_4^+$), and 531 (M$^+$).

EXAMPLE 2

G1-COO—Eu (2)

Europium 3,5-Di[4'-(2"-ethylhexyloxy)phenyl]benzoate

A mixture of G1-COOH (1) (500 mg, 0.942 mmo), freshly dried Eu(OAc)$_3$.3H$_2$O (70° C., 0.5 mbar overnight) (103 mg, 0.314 mmol) and 28 cm$^3$ of chlorobenzene was heated (bath temperature 70-75° C.) under reduced pressure (water aspirator). The solvent was removed slowly over 1.5 h and the residue was evaporated under vacuum to leave a pale yellow oil. The oil was then triturate with MeOH to leave a light yellow solid. The solid was then dried over vacuum (0.5 mbar overnight) to give 552 mg (100%) of a yellowish solid of europium complex 2; (Found: C, 71.7; H, 7.9. for $C_{105}H_{135}EuO_{12}$ requires C, 72.4; H, 7.8%; for $C_{105}H_{137}EuO_{13}$ requires C, 71.7; H, 7.9%); $\lambda_{max}$/nm (thin film) 268, and 328.

EXAMPLE 3

G1-COO—Tb (3)

Terbium 3,5-Di[4'-(2"-ethylhexyloxy)phenyl]benzoate

A mixture of G1-COOH (1) (500 mg, 0.942 mmol), freshly dried Tb(OAc)$_3$.3H$_2$O (70° C., 0.5 mbar overnight) (105 mg, 0.314 mmol) and 28 cm$^3$ of chlorobenzene was heated (bath temperature 70-75° C.) under reduced pressure (water aspirator). Most of the solvent was slowly removed over 1.5 h and the residue was dried under vacuum to leave a pale yellow oil. The oil was then triturate with MeOH to leave a light yellow solid. The solid was then dried under vacuum (0.5 mbar overnight) to give 548 mg (100%) of a yellowish solid of the desired terbium complex 3; (Found: C, 71.9; H, 7.6. for $C_{105}H_{135}TbO_{12}$ requires C, 72.1; H, 7.8%; for $C_{105}H_{137}TbO_{13}$ requires C, 71.4; H, 7.8%); $\lambda_{max}$/nm (thin film) 270, and 330.

General procedure for the complexation of co-ligands with G1-COO-Ln (can be used for Eu & Tb)

A mixture of the europium complex 2 (6.0 mg, 0.003 mmol), 2,2'-bipyridyl (0.5 mg, 0.003 mmol,) and 0.2 cm$^3$ of toluene was stirred for 10 min to give a clear/homogeneous solution. The solution was filtered through a cotton wool before being spin-coated on a quartz substrate at 1500 rpm for 60 sec;

G1-COO—Eu.2,2'-dipyridyl; $\lambda_{max}$/nm (thin film) 268, and 329;

G1-COO—Eu.4,4'-di-tert-butyl-2,2'-bipyridyl; $\lambda_{max}$/nm (thin film) 268, and 327;

G1-COO—Eu.4,4'-di-tert-butyl-2,2'-bipyridyl di-N-oxide; $\lambda_{max}$/nm (thin film) 267, and 323;

G1-COO—Eu.1,10-phenanthroline; $\lambda_{max}$/nm (thin film) 268, and 329;

G1-COO—Eu.1,10-phenanthroline N-oxide; $\lambda_{max}$/nm (thin film) 268, and 329;

G1-COO—Eu.bathocuproin; $\lambda_{max}$/nm (thin film) 271, and 329;

G1-COO—Tb.4,4'-di-tert-butyl-2,2'-bipyridyl di-N-oxide; $\lambda_{max}$/nm (thin film) 267, and 326;

G1-COO—Tb.1,10-phenanthroline; $\lambda_{max}$/nm (thin film) 270, and 326;

G1-COO—Tb.1,10-phenanthroline N-oxide; $\lambda_{max}$/nm (thin film) 270, and 326;

G1-COO—Tb.bathocuproin; $\lambda_{max}$/nm (thin film) 270, and 329.

EXAMPLE 4

2-(4'-BrPh)Py

2-(4'-Bromophenyl)pyridine

A mixture of 2-bromopyridine (1.22 g, 7.69 mmol), 4-bromophenylboronic acid (2.00 g, 10.0 mmol), tetrakis(triphenylphosphine)palladium (0) (622 mg, 0.538 mmol), 2 M Na$_2$CO$_{3(aq)}$ (8 cm$^3$), EtOH (8 cm$^3$) and toluene (22 cm$^3$) was degassed and then heated at reflux (with bath temperature 105° C.) under argon for 17 h. The reaction was allowed cool. Water (10 cm$^3$) and ether (10 cm$^3$) were added to the mixture. The two phases were separated. The aqueous layer was extracted with ether (3×10 cm$^3$). The organic layer and the ether extracts were combined, washed with brine (1×30 cm$^3$) and dried over anhydrous magnesium sulfate. The solvents were completely removed. The residue was purified by column chromatography of silica gel using light petroleum (60-80° C.) to give 1.52 g (84%) of 4 as a colourless solid as the desired product; mp 62° C.;$^{ref}$ (E. C. Butterworth, I. M. Heibron and D. H. Hey, *J. Chem. Soc.*, 1940, 355) $\delta_H$(200 MHz; CDCl$_3$) 7.23-7.35 (1H, m, PyH), 7.58-7.67 (2H, m, ArH), 7.68-7.81 (2H, m, PyH), 7.83-7.93 (2H, m, ArH), and 8.69 (1H, m, PyH). The $^1$H NMR is similar to the reported by M. A. Gutierrez, G. R. Newkome, J. Selbin, *J. Organomet. Chem.*, 1980, 202, 341-350

EXAMPLE 5

2-(4'-G1-Ph)Py 2-(4'-{3",5"-Di[4"'-(2""-ethylhexyloxy)phenyl]phenyl}phenyl)pyridine A mixture of the boronic compound of Reference Example 6: (G1-BX$_2$) (1.18 g, 2.22 mmol), 2-(4'-bromophenyl)pyridine (400 mg, 1.71 mmol), tetrakis(triphenylphosphine)palladium (0) (138 mg, 0.120 mmol), 2 M Na$_2$CO$_{3\ (aq)}$ (1.8 cm$^3$), EtOH (1.8 cm$^3$) and toluene (5.0 cm$^3$) was degassed and then heated at reflux (with bath temperature of 103° C.) under argon for 16 h. The mixture was allowed to cool and then diluted with water (4 cm$^3$) and ether (5 cm$^3$). The two phases were separated. The aqueous layer was extracted with ether (3×10 cm$^3$). The organic layer and the ether extracts were combined and dried over anhydrous sodium sulfate. The solvents were completely removed to give 1.5 g of crude product. The residue was purified by column chromatography over silica gel using ethyl acetate-light petroleum (0:1 to 1:10) as eluent to give 1.04 g (95%) of 5 as a white solid; (Found: C, 84.1; H, 8.3; N, 2.3. C$_{45}$H$_{53}$NO$_3$ requires C, 84.5; H, 8.4; N, 2.2%); $\lambda_{max}$/nm (thin film) 286; $\delta_H$(400 MHz; CDCl$_3$) 0.89-1.03 (12H, Me), 1.32-1.67 (16H, m, CH$_2$), 1.77-1.88 (2H, CH), 3.93 (4H, m, ArOCH$_2$), 7.05 (4H, ArH), 7.25-7.28 (1H, m, PyH), 7.66 (4H, m, ArH), 7.75-7.85 (7H, m, ArH & PyH), 8.15 (2H, ArH), and 8.76 (1H, m, PyH); $\delta_C$(101 MHz; CDCl$_3$) 11.1, 14.1, 23.1, 23.9, 29.1, 30.5, 39.4, 70.5, 114.8, 120.5, 122.2, 124.3, 127.3, 127.7, 128.3, 133.4, 136.8, 138.4, 141.6, 141.8, 142.1, 149.7, 157.0, 159.2, m/z [APCI$^+$] 640 (M$^+$).

EXAMPLE 6

2-(3'-BrPh)Py 2-(3'-Bromophenyl)pyridine

A mixture of 2-bromopyridine (2.40 g, 15.3 mmol), 3-bromophenylboronic acid (4.00 g, 19.9 mmol), tetrakis(triphenylphosphine)palladium (0) (1.24 g, 1.07 mmol), 2 M Na$_2$CO$_{3(aq)}$ (16 cm$^3$), EtOH (16 cm$^3$) and toluene (44 cm$^3$) was degassed and heated at reflux (with bath temperature 106° C.) under argon for 17 h. The reaction was allowed to cool to give an yellow orange mixture. The mixture was diluted with water (10 cm$^3$) and ether (20 cm$^3$). The two phases were separated. The aqueous layer was extracted with ether (3×15 cm$^3$). The organic layer and the ether extracts were combined and dried over anhydrous sodium sulfate. The solvents were completely removed to leave an orange oil. The oil was purified by column chromatography over silica gel using ethyl acetate-light petroleum (0:1 to 1:10) as eluent to give 2.86 g (80%) of 6 as a pale yellow oil; $\delta_H$(200 MHz; CDCl$_3$) 7.18-7.40 (2H, m, PyH & ArH), 7.55 (1H, m, ArH), 7.66-7.85 (2H, m, PyH), 7.92 (1H, m, ArH), 8.17-8.19 (1H, m, ArH), and 8.71 (1H, m, PyH). The $^1$H NMR is similar to the reported by M. van der Sluis, V. Beverwijk, A. Termaten, F. Bickelhaupt, H. Kooijman, A. L. Spek, *Organometallics*, 1999, 18, 1402-11407.

EXAMPLE 7

2-(3'-G1-Ph)Py 2-(3'-{3",5"-Di[4"'-(2""-ethylhexyloxy)phenyl]phenyl}phenyl)pyridine A mixture of the boronic compound of Reference Example 6: (G1-BX$_2$) (455 mg, 0.858 mmol), 2-(3'-bromophenyl)pyridine (154 mg, 0.659 mmol), tetrakis(triphenylphosphine) palladium (0) (54 mg, 0.046 mmol), 2 M Na$_2$CO$_{3(aq)}$ (0.7 cm$^3$), EtOH (0.7 cm$^3$) and toluene (2.0 cm$^3$) was degassed and heated at reflux (with bath temperature of 103° C.) under argon for 17 h. The mixture was allowed to cool and passed through a plug of silica gel using ether as eluent. The filtrate was collected and the solvents were completely removed to leave an orange oil. The oil was purified by column chromatography over silica gel using ethyl acetate-light petroleum (0:1 to 1:10) as eluent to give 362 mg (86%) of 7 as a colourless oil; (Found: C, 84.2; H, 8.5; N, 2.2. C$_{45}$H$_{53}$NO$_2$ requires C, 84.5; H, 8.4; N, 2.2%); $\lambda_{max}$/nm (thin film) 270; $\delta_H$(400 MHz; CDCl$_3$) 0.90-1.03 (12H, m, Me), 1.32-1.67 (16H, m, CH$_2$), 1.79-1.86 (2H, CH), 3.95 (4H, m, ArOCH$_2$), 7.06 (4H, ArH), 7.23-7.31 (1H, m, PyH), 7.62 (1H, m, ArH), 7.68 (4H, m, ArH), 7.75-7.88 (6H, m, PyH & ArH), 8.05 (1H, m, ArH), 8.37 (1H, m, ArH), and 8.77 (1H, m, PyH); $\delta_C$(101 MHz; CDCl$_3$) 11.5, 14.1, 23.1, 23.8, 29.1, 30.5, 39.4, 70.5, 114.8, 120.8, 122.3, 124.3, 124.5, 126.0, 128.0, 128.3, 129.2, 133.4, 136.8, 140.0, 141.94, 141.97, 142.1, 149.7, 157.4, 159.2, and 164.3; m/z [APCI$^+$] 640 (M$^+$).

EXAMPLE 8

(2-PhPy)[2-(3'-BrPh)Py]$_2$Ir (2-Phenylpyridine)-bis[2-(3'-bromophenyl)pyridine] iridium (III)

A mixture of the 2-(3'-bromophenyl)pyridine (367 mg, 1.57 mmol), iridium chloride tri-hydrate (124 mg, 0.352 mmol), H$_2$O (3.0 cm$^3$) and 2-ethoxyethanol (10 cm$^3$) was heated (bath temperature: 130° C.) under argon for 23 h before being cooled. A bright yellow solid precipitated from the mixture. The solid was filtered, washed with 95% of EtOH (20 cm$^3$) and dried to give 197 mg. The resultant was passed through a silica gel column using ethyl acetate-light petroleum (0:1 to 1:10), DCM and then MeOH as eluent. The filtrate was collected (~600 cm$^3$) and concentrated to about 50 cm$^3$. An orange yellow solid precipitated and was collected by filtration. The filter cake was washed with MeOH (~10 cm$^3$). The bright yellow solid was dried to give 177 mg; $\delta_H$(200 MHz; CDCl$_3$) 5.74 (2H, d, J 8.4 Hz, ArH), 6.70 (2H, ArH), 6.78-6.79 (2H, m, PyH), 7.62 (2H, d, J 2.0 Hz, ArH), 7.74-7.93 (4H, m, PyH), and 9.19 (2H, d, J 5.8 Hz, PyH); m/z [APCI$^+$] 659 ($C_{22}H_{14}Br_2IrN_2^+$).

A mixture of the iridium complex and 2-phenylpyridine (738 mg, 4.756 mmol) and silver trifluoromethanesulfonate (82 mg, 0.317 mmol) was heated (bath temperature: 130-140° C.) for 4.0 days under argon. The reaction was then allowed to cool to room temperature to give a brown yellow precipitate. The solid was washed with ethanol (10 cm$^3$) and dried. The residue was further purified by column chromatography over silica gel with DCM as eluent to give 100 mg (78%) of 8 as an orange yellow solid; $\lambda_{max}$(thin film)/nm 248, 297, and 389; $\delta_H$(200 MHz; CDCl$_3$) 6.65-0.98 (11H, m, ArH and/or PyH), and 7.45-7.93 (11H, ArH and/or PyH); m/z [APCI$^+$] 814 (MH$^+$).

EXAMPLE 9

(2-PhPy)[2-(3'-G1-Ph)Py]$_2$Ir (2-Phenylpyridine)-bis[2-(3'-{3",5"-di[4'''-(2''''-ethylhexyloxy)phenyl]phenyl}phenyl)pyridine]iridium (III)

A mixture of the boronic compound Reference Example 6: (G1-BX$_2$) (196 mg, 0.369 mmol), 8 (100 mg, 0.123 mmol), tetrakis(triphenylphosphine)palladium (0) (10 mg, 0.009 mmol), 2 M Na$_2$CO$_{3(aq)}$ (0.3 cm$^3$), EtOH (0.3 cm$^3$) and toluene (1.0 cm$^3$) was degassed and heated at reflux (with bath temperature of 103° C.) under argon for 44 h. The mixture was allowed to cool and purified by column chromatography over silica gel using ethyl acetate-light petroleum (1:10) and then DCM-light petroleum (1:4) as eluent, to give ≅18 mg (≅9%) of 9 as an orange solid; $\lambda_{max}$/nm (thin film) 279 and 390; $\delta_H$(200 MHz; CDCl$_3$) 0.83-1.02 (24H, m, Me), 1.23-1.64 (32H, m, CH$_2$), 1.68-1.88 (4H, m, CH), 3.90 (8H, m, ArOCH$_2$), 6.88-7.09 (17H, m, ArH and/or PyH), 7.24-7.27 (1H, m, ArH and/or PyH), 7.57-7.75 (21H, ArH and/or PyH), and 7.89-8.03 (5H, m, ArH and/or PyH).

EXAMPLE 10

Fac[2-(4'-G1-Ph)Py]$_3$Ir

Fac tris[2-(4'-{3",5"-di[4'''-(2''''-ethylhexyloxy)phenyl]phenyl}phenyl)pyridine]iridium (III)

A mixture of the 2-(4'-G1-Ph)Py 5 (490 mg, 0.766 mmol), iridium chloride tri-hydrate (68 mg, 0.191 mmol), H$_2$O (1.6 cm$^3$) and 2-ethoxyethanol (4.9 cm$^3$) was heated (bath temperature: 130° C.) under argon for 28 h before being cooled. The resultant mixture was passed through a silica gel column using ethyl acetate-light petroleum (0:1 to 1:10) and then DCM as eluents. The solvents were completely removed. The residue was dissolved in ~2 cm$^3$ of DCM and ~2 cm$^3$ of MeOH was added and the mixture was cooled. The precipitate was collected (about 238 mg) and used without further purification for the next step. The mother liquid was concentrated to recycle the unreacted 5 (about 244 mg).

A mixture of the above obtained iridium complex, recycled ligand 5 (about 244 mg), 2-(4'-G1-Ph)Py 5 (200 mg, 0.313 mmol) and silver trifluoromethanesulfonate (70 mg, 0.272 mmol) was heated (with bath temperature of 130-140° C.) for 88 h under argon. The reaction was then allowed to cool to room temperature and ~5 cm$^3$ of DCM was added. The brown yellow mixture was purified by column chromatography over silica gel with DCM-ethyl acetate-light petroleum (0:1:10 to 1:1:10) as eluent to give 200 mg (49% for two steps referring to IrCl$_3$.3H$_2$O) of 10 as an orange yellow solid; TGA$_{(5\%)}$ 410° C.; (Found: C, 76.8; H, 7.5; N, 2.0. $C_{135}H_{156}IrN_3O_6$ requires C, 76.9; H, 7.5; N, 2.0%); $\lambda_{max}$/nm (thin film) 277, and 397; $\delta_H$(200 MHz; CDCl$_3$) 0.78-1.03 (36H, m, Me), 1.15-1.50 (48H, m, CH$_2$), 1.52-1.72 (6H, m, CH), 3.65 (12H, m, ArOCH$_2$), 6.58 (12H, m, ArH), 6.92 (3H, t, J 6.4 Hz, PyH), and 7.32-7.92 (39H, m, ArH & PyH); m/z [MALDI] 2105, 2106, 2107, 2108, 2109, 2110, 2111, 2112, 2113 (M$^+$).

EXAMPLE 11

Fac[2-(3'-G1-Ph)Py]$_3$Ir

Fac tris[2-(3'-{3",5"-di[4'''-(2''''-ethylhexyloxy)phenyl]phenyl}phenyl)pyridine]iridium (III)

A mixture of the 2-(3'-G1-Ph)Py 7 (294 mg, 0.459 mmol), iridium chloride tri-hydrate (41 mg, 0.115 mmol), H$_2$O (1.0 cm$^3$) and 2-ethoxyethanol (3.0 cm$^3$) was heated (bath temperature: 125-135° C.) under argon for 39 h before being cooled. The resultant mixture was passed through a silica gel column using ethyl acetate-light petroleum (0:1 to 1:10), DCM and then MeOH as eluents. The filtrate was collected (~600 cm$^3$) and concentrated to about 50 cm$^3$. An orange yellow solid precipitated and was collected by filtration. The residue was washed with MeOH (~10 cm$^3$). The bright yellow solid was dried (177 mg). The residue was precipitated using DCM and MeOH (3 cm$^3$) to give a yellow solid (125 mg) of impure iridium complex. Meanwhile, the excess of 2-(3'-G1-Ph)Py 7 was collected from the mother liquor. The two products were used without further purification for the next step. A mixture of the above obtained iridium complex and recycled 2-(3'-G1-Ph)Py 7 and silver trifluoromethanesulfonate (34 mg, 0.133 mmol) was heated (bath temperature: 130° C.) for 3.5 days under argon. The reaction was then allowed to cool to room temperature. The brown yellow mixture was purified on silica gel column with eluent of DCM-ethyl acetate-light petroleum (0:1:10 to 1:1:10) as eluent to give 95 mg (39% for two steps referring to IrCl$_3$.3H$_2$O) of orange yellow solid as 11; TGA$_{(5\%)}$ 400° C.; (Found: C, 76.7; H, 7.2; N, 2.1. $C_{135}H_{156}IrN_3O_6$ requires C, 76.9; H, 7.5; N, 2.0%); $\lambda_{max}$/nm (thin film) 279 and 390; $\delta_H$(400 MHz; CD$_2$Cl$_2$) 0.92-1.07 (36H, m, Me), 1.31-1.66 (48H, m, CH$_2$), 1.73-1.86 (6H, m, CH), 3.95 (12H, m, ArOCH$_2$), 7.00-7.13 (18H, m, ArH & PyH), 7.30 (3H, m, ArH) 7.62-7.83 (27H, m, ArH & PyH), 8.10 (3H, m, ArH), and 8.15 (3H, m, PyH); $\delta_C$(101 MHz; CDCl$_3$) 10.8, 14.7, 23.9, 24.6, 29.9, 31.3, 40.2, 71.35, 115.5, 120.0, 123.4, 123.6, 123.8, 124.2, 129.0, 129.7, 134.0, 134.3, 137.4, 138.1, 142.5, 144.1, 145.4, 148.2, 160.0, and 167.0; m/z [MALDI] 2105, 2106, 2107, 2108, 2109, 2110, 2111, 2112, 2113 (M$^+$).

EXAMPLE 12

G1-Pt-Porphyrin 5,10,15,20-Tetra[3',5'-di(3",5"-di-tert-butylstyryl) phenyl]porphyrinato platinum (II) (12)

5,10,15,20-Tetra[3',5'-di(3",5"-di-tert-butylstyryl)phenyl] porphyrin (WO 99/21935: 1-Porphyrin: First/Second Example) (50.0 mg, 21.5 mmol) was added to a refluxing solution of platinum (II) chloride (11.4 mg, 42.9 mmol) in benzonitrile (1 cm$^3$). The solution was heated at reflux under a stream of nitrogen to remove the evolved hydrogen chloride for 1 h. The solvent was removed under vacuum. Column chromatography over silica, eluting with DCM-light petroleum (1:3) was performed. Impure fractions were combined and further purified by column chromatography with DCM-light petroleum (1:4) as eluent. The combined material was recrystallised from a DCM-MeOH mixture to give 42.0 mg (77%) of 12 as a brick-red solid; mp>295° C. (decomp.) (Found: C, 81.6; H, 7.9; N, 2.1. $C_{172}H_{204}N_4Pt$ requires C, 81.9; H, 8.2; N, 2.2%); $v_{max}$ (KBr)/cm$^{-1}$ 1594 (C=C), and 959 (C=C—H trans); $\lambda_{max}$(CHCl$_3$)/nm (log $\epsilon$/dm$^3$mol$^{-1}$ cm$^{-1}$) 309 (5.43), 328 sh (5.30), 413 (5.64), 514 (4.60), and 544 (4.21); $\delta_H$(400 MHz, CDCl$_3$) 1.35 (144H, s, t-Bu), 7.36-7.43 (40H, m, ArH & vinyl H), 8.11 (4H, hr s, ArH), 8.29 (8H, d, J 1.0 Hz, ArH), and 8.97 (8H, s, b-pyrrolic H); m/z [MALDI] 2523 (MH$^+$).

EXAMPLE 13

G2-Pt-Porphyrin 5,10,15,20-Tetra[3',5'-di(3",5"-di(3"',5"'-di-tert-butyl-styryl)styryl)phenyl]porphyrinato platinum (I) (13)

5,10,15,20-Tetra[3',5'-di(3",5"-di(3"',5"'-di-tert-butyl-styryl)styryl)phenyl]porphyrin (WO 99/21935: 2-Porphyrin: First/Second Example) (50.0 mg, 10.3 mmol) was added to a refluxing solution of platinum (II) chloride (21.3 mg, 80.1 mmol) in benzonitrile (1.0 cm$^3$), and washed in with further benzonitrile (1.0 cm$^3$). The mixture was heated at reflux under a stream of nitrogen to remove the evolved hydrogen chloride for 2.5 h. The solvent was removed and the residue was purified by column chromatography with DCM-light petroleum (1:4) as eluent to give 36.8 mg (71%) of 13 as an orange solid; $\delta_H$(200 MHz, CDCl$_3$) 1.31 (288H, s, t-Bu), 7.18-7.65 (120H, m, vinyl H & ArH), 8.23 (4H, s, ArH), 8.34 (8H, s, ArH), and 9.05 (8H, s, b-pyrrolic H).

Device Fabrication

LEDs were fabricated by the following method. Patterned indium tin oxide (ITO) substrates were cleaned with acetone and 2-propanol in an ultrasound bath. A hole injecting layer of PEDOT (Bayer) was then spin-coated from water at 1000 rpm onto the cleaned ITO substrate and dried at 80° C. on a hot plate for 5 minutes. Dendrimer solutions were subsequently spin-coated onto the PEDOT layer at speeds of 800 rpm to give films typically 100 nm thick, and an aluminium cathode was then evaporated giving devices with active areas of 2 mm$^2$. Device testing was performed in vacuum using a Keithley source measure unit for dc operation as well as a Hewlett Packard pulse generator (rise time <10 ns) for pulsed operation. The RC value of the devices, defining the time required for charging the LED, was estimated to be in the order of 100 ns and driving conditions were chosen appropriately. The emission spectra were measured using an ISA Spectrum One CCD spectrometer. PL and PL excitation (PLE) spectra were obtained on an ISA Fluoromax fluorimeter. All emission spectra were corrected for the instrument response. As a crosscheck, PL spectra were also recorded on the CCD and found to be identical to those obtained on the fluorimeter.

EXAMPLE 14

Device Results for G1-Pt-porphyrin 12

Films and LED devices were made using 12 blended with either dendrimer A or dendrimer B (FIG. 9). Films of 12/host blends were formed by spin-coating THF solutions of the two dendrimers (10 mg/ml) in a w/w ratio of host to guest of 10:1 corresponding to a molar ratio of approximately 3:1. No phase separation was observed with these spin-coated films and their absorption was found to be a sum of the components. The films of the blends appeared to be of comparable quality to films prepared of the individual materials The synthesis of A is described in Reference Example 7 taken together with Reference Examples 7A to 7C and 8.

Dendrimer B was obtained as follows:

1,3,5-Tris[(4'-formylstyryl)phenyl]benzene

A mixture of 4-vinylbenzaldehyde (1.95 g, 14.7 mmol), N,N-dimethylacetamide (40 mL), 1,3,5-tris(4'-bromophenyl) benzene (2.00 g, 3.68 mmol), trans-di(µ-aceto)-bis[o-(di-o-tolylphosphino)benzyl]dipalladium (II) (10 mg, 11 µmmol), 2,6-di-tert-butyl-p-cresol (646 mg, 29.3 mmol), and sodium carbonate (1.56 g, 14.7 mmol) was deoxygenated by sequential evacuation and purging with argon over 35 min. The mixture was then stirred at 130° C. for 50.5 h. Water (100 mL) and dichloromethane (100 mL) were added. The aqueous layer was separated and extracted with dichloromethane (3×100 mL, 2×50 mL, 2×100 mL). The combined organic layers were washed with water (3×500 mL) and brine (250 mL), dried over anhydrous sodium sulfate, filtered and the solvent completely removed to leave a yellow/brown solid. Trituration with dichloromethane followed by recrystallisation from dichloromethane gave 1,3,5-Tris[(4'-formylstyryl) phenyl]benzene (1.24 g, 48%) as a yellow powder, mp 163° C. Anal. Calcd for $C_{51}H_{36}O_3$: C, 87.9; H, 5.2. Found: C, 87.4; H, 5.4. $v_{max}$ (KBr)/cm$^{-1}$ 1690 (C=O) and 962 (C=C—H trans). $\lambda_{max}$(CH$_2$Cl$_2$)/nm: 358 (log $\epsilon$/dm$^3$mol$^{-1}$cm$^{-1}$ 5.10). $\delta_H$(500 MHz, CDCl$_3$) 7.24 and 7.35 (6H, d, J=16.5 Hz, vinylic H), 7.69 (6H, ½AA'BB', cp H), 7.77 (6H, ½AA'BB', cp H), 7.71 (6H, ½AA'BB', cp H), 7.86 (3H, s, cep H), 7.91 (6H, ½AA'BB', cp H) and 10.0 (3H, s, CHO); m/z (CI) 697.0 (MN$^+$, 100%).

[G-3]$_3$B 9 B

Potassium-tert-butoxide (171 mg, 1.52 mmol) was added to a solution of 1,3,5-Tris[(4'-formylstyryl)phenyl]benzene (51.5 mg, 0.07 mmol), Reference example 7A (759 mg, 0.30 mmol) in dry tetrahydrofuran (20 mL) heated at reflux. The solution was heated at reflux for 18 h and then allowed to cool. Water (50 mL) and dichloromethane (50 mL) were added and the organic layer separated. The aqueous layer was extracted with dichloromethane (50 mL) and then brine (50 mL) was added to the aqueous layer before a final extraction with dichloromethane (50 mL). The combined organic layers were washed with brine (50 mL), dried over anhydrous sodium sulfate, filtered, and the solvent removed. The residue was purified by column chromatography over silica in two steps. The first chromatographic step used a dichloromethane/light petroleum mixture (2:3) as eluent and the main fraction was collected and the solvent removed. The residue was further purified using a dichloromethane/light petroleum mixture (3:7 to 2:3) as eluent to give B (349 mg, 60%). Further purification by recrystallisation from a dichloromethane/ methanol mixture gave a yellow oil which was then triturated with methanol to give a powder, mp decomp 281° C. Anal. Calcd for $C_{600}H_{690}$: C, 91.2; H, 8.8. Found: C, 91.7; H, 9.1. $v_{max}$(KBr)/cm$^{-1}$ 958 (C=C—H trans). $\lambda_{max}$(CH$_2$Cl$_2$)/nm: 323 (log $\epsilon$/dm$^3$mol$^{-1}$cm$^{-1}$ 6.06), 377 sh (5.46) and 400 sh (5.22). $\delta_H$(400 MHz, CDCl$_3$) 1.40 (432H, s, t-butyl H), 7.18-7.45 (96H, cv H, G-1 vinyl H, G-2 vinyl H and G-3 vinyl H), 7.40 (24H, dd, J=1.5, sp H), 7.46 (48H, d, J=1.5, sp H), 7.62-7.82 (87H, cp H, G-1 bp H, G-2 bp H and G-3 bp H) and 7.90 (3H, s, cep H); m/z (MALDI) 7905.2 (MH$^+$, 100%); Calc MR$^+$ 7903.1.

Figure 10:
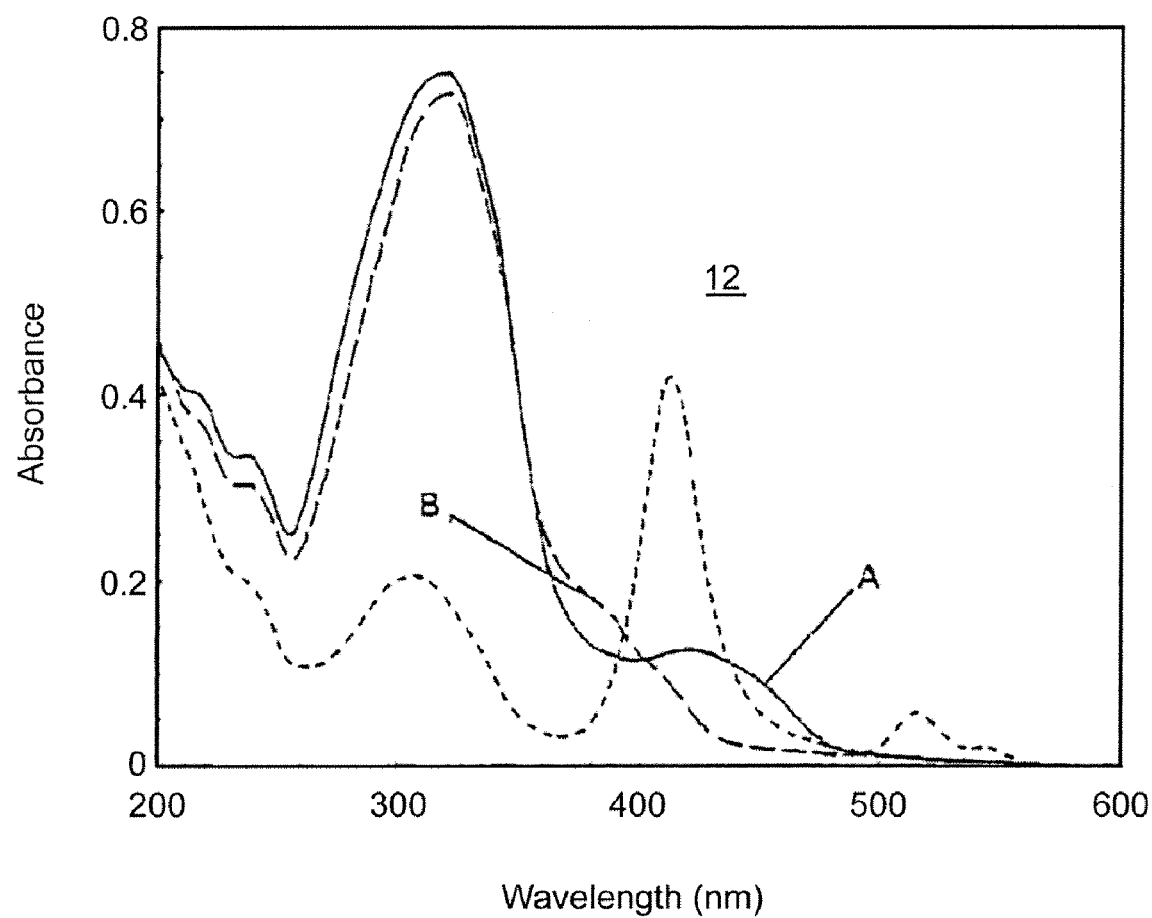
FIG. 10 shows film absorption spectra of neat dendrimer films (A, B and 12)

The absorption spectra of the materials A, B and 12 are shown in FIG. 10. For A, B and 12 the stilbene moieties are found to give rise to an absorption peak at 320 nm. In A the core gives rise to an additional absorption at 420 nm, whilst in B the core gives rise to an absorption at 370 nm and for 12 absorption bands are observed at 420 nm, 514 nm and 544 nm, corresponding to the Soret and Q-bands of the G1-Pt-porphyrin 12.

Figure 11:
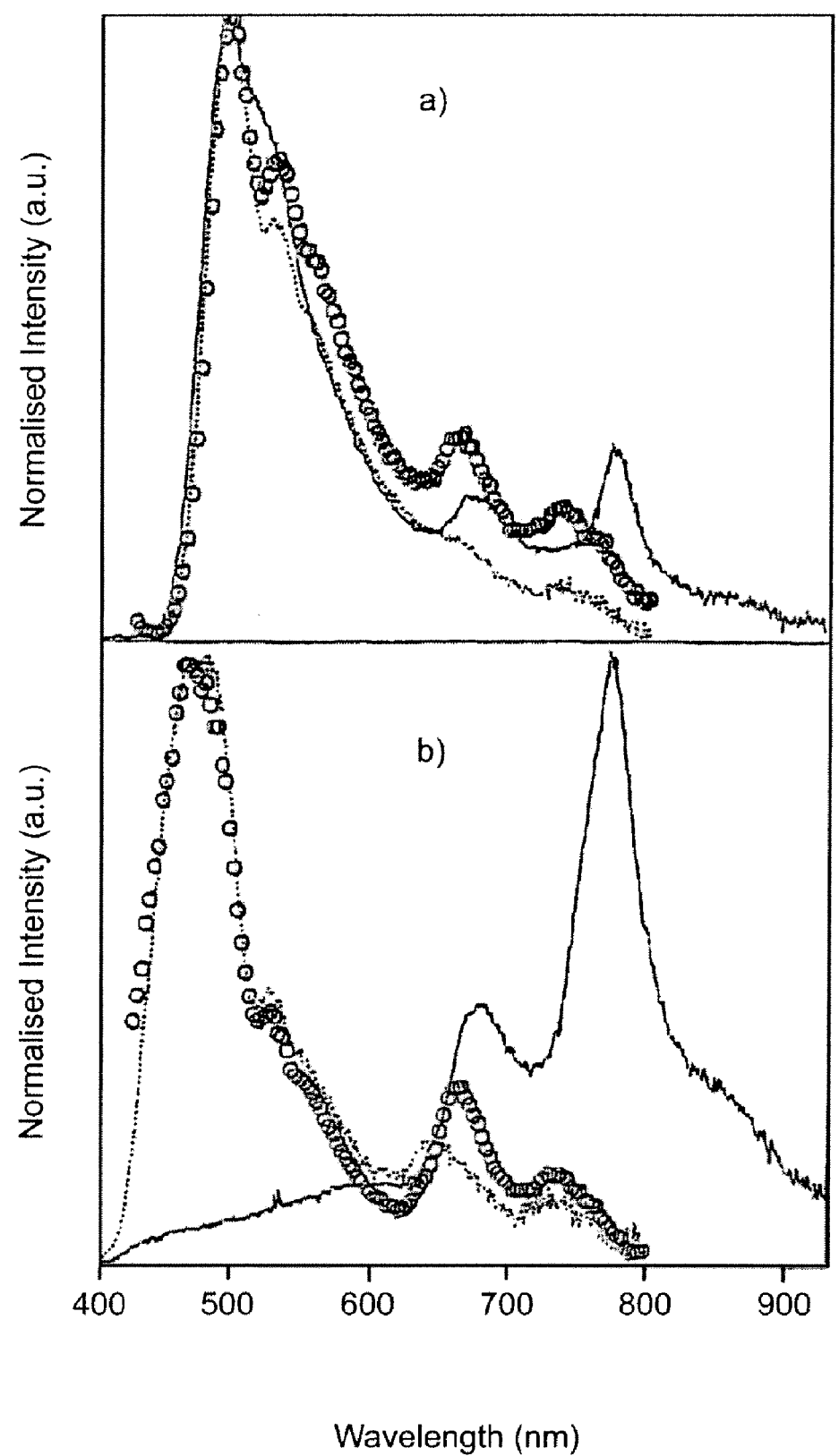
FIG. 11 shows luminescence of films of dendrimer A and B doped with guest dendrimer 12 in both EL and PL, a) Blend A:12 PL excited at 320 nm ( . . . ) PL excited at 420 nm (°) and EL (—) b) Blend of B:12, PL excited at 320 nm ( . . . ) PL excited at 420 nm (°) and EL (—)

FIG. 11 shows PL and EL spectra of blends of the materials under continuous excitation. Upon optical excitation, the emission of A appears green and peaks at 495 nm, whereas the emission of B is in the blue and peaks at 470 nm, and in both blends the guest dendrimer 12 emits in the red to near IR with peaks at 662 nm and 737 nm. The emission of the host dendrimers A and B is attributed to fluorescence, whereas the emission of the guest 12 is believed to be due to phosphorescence. For both the A:12 and B:12 blends the host PL emission is much stronger than the guest PL emission.

The most surprising result illustrated in FIG. 11 is the large difference between EL spectra of the blend B:12 compared to the PL spectra. In contrast to the PL, in EL the guest emission is very much stronger than the host emission in the B:12 blend. For the A:12 blend there is also an increase in the guest to host emission in the EL relative to the PL, although the increase is less marked than in the case of the B:12 blend. The differences between the EL and PL spectra are due to charge trapping in the EL devices, which affects where recombination occurs. In both blends there is a red shift in the guest EL emission compared with the PL emission. The devices can be driven continuously or by pulse driving. It was also found that there is a dependence of the emission spectrum on the driving conditions and the duty cycle.

EXAMPLE 15

Device results for Ir dendrimer [2-(4'-G1-Ph)Py]$_3$Ir 10

Devices containing the novel Ir dendrimer 10 were fabricated using the standard method described above. Devices were made with a neat Ir dendrimer layer and with a layer containing the Ir dendrimer blended with a mixture of dendrimer B and PBD (2-(4-biphenylyl)-5-(4-tert-butylphenyl)-1,3,4-oxadiazole)). The structures of the two types of device were:
  ITO/PEDOT/10 (40 nm)/Al
  ITO/PEDOT/dendrimer B: 10:PBD/Al
where in the blend the ratio of dendrimer B:10:PBD is 1:0.1:0.4 by weight, and two devices were formed one with a blended layer thickness of 150 nm and the other with a blended layer 200 nm thick.

Figure 12:
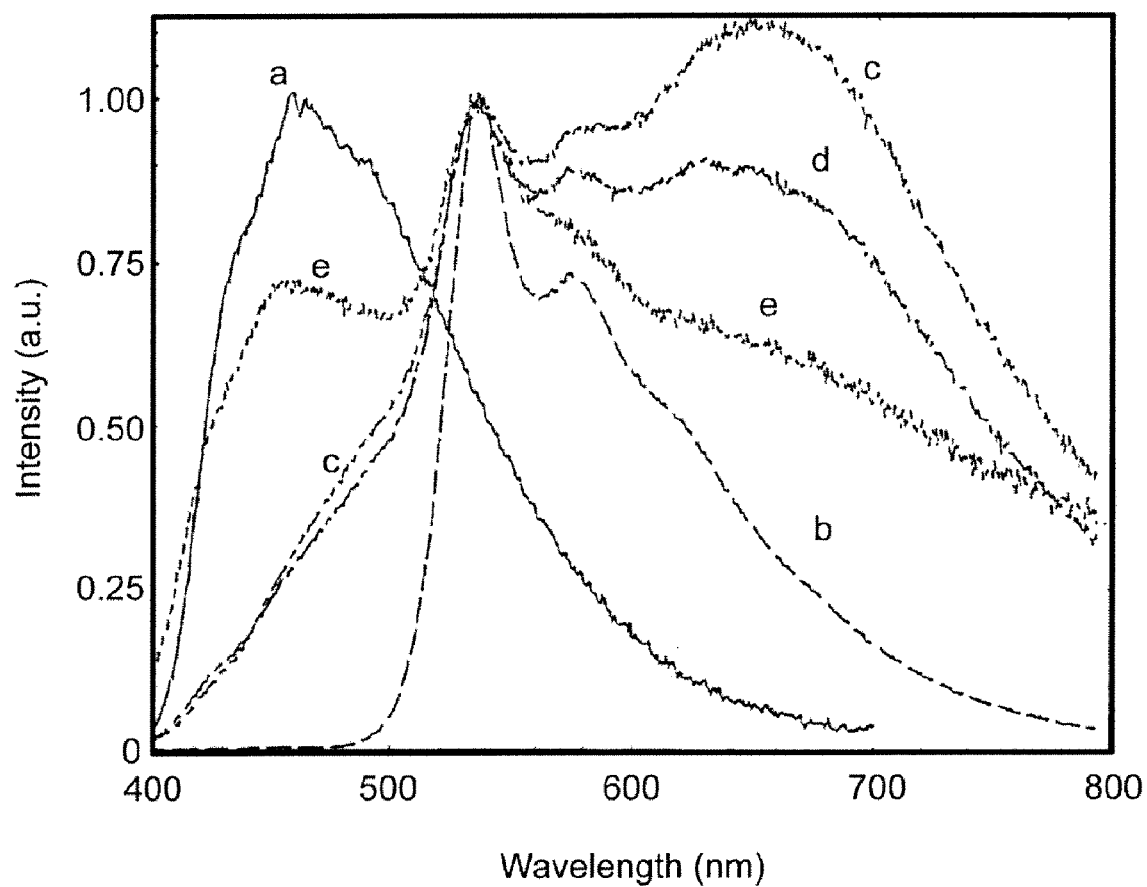
FIG. 12 shows EL spectra of host (B), guest (10) and blends under different operating conditions. Neat host emission (a), neat guest emission (b), 200 nm blend device pulsed (c), 200 nm blend device steady state (d) 150 nm blend device steady state (e)

The emission spectra of the neat materials as well as the blends are shown in FIG. 12. The iridium dendrimer (10) exhibits broad EL in the green (peak at 535 nm with features at 577 nm and 623 nm). The benzene cored dendrimer (B) emits in the blue (peak at 460 nm). In blends both the host and the guest emit. The EL spectrum of the blend is not a mere superposition of the guest and host. In the thicker device, the emission band of the host cannot be identified, yet there is significant unstructured emission below the band of the iridium dendrimer. Most significantly, a new emission band is observed at 660 nm, which forms the emission maximum in some cases. This band is not immediately visible in neat 10 devices.

The blend EL spectra appeared white whereas PL spectra of films were green. This suggests that the broad feature formed in EL at 660 nm be not due to an exciplex but rather due to an intermolecular charge transfer state formed between host and guest. A strong dependence of the emission spectrum on the driving conditions is observed, indicating that the emission consists of both phosphorescent and fluorescent components.

EXAMPLE 16

Device results for iridium dendrimer [2-(3'-G1-Ph)Py]$_3$Ir (11)

Figure 13:
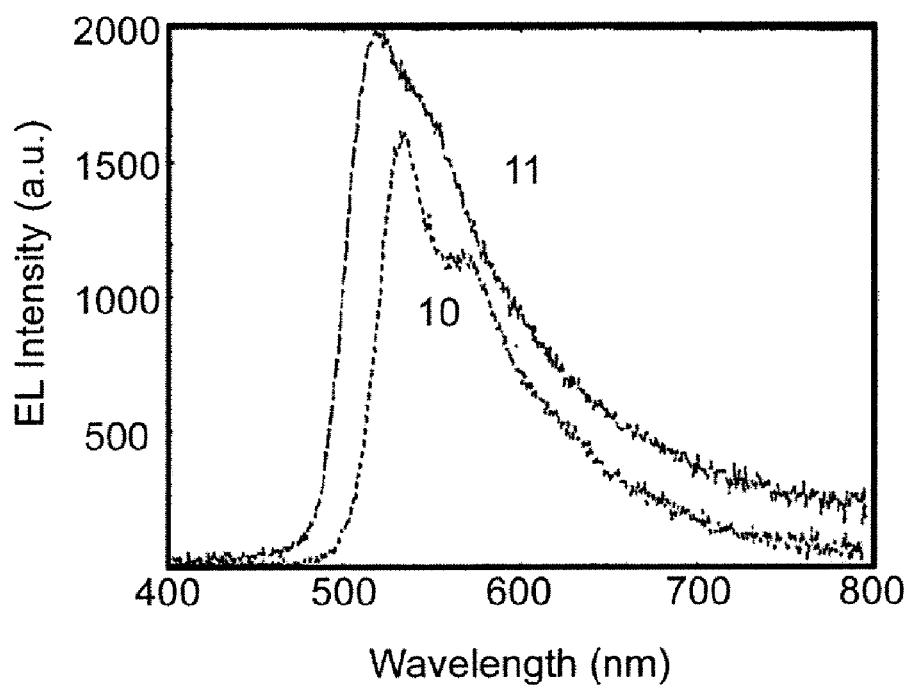
FIG. 13 shows the EL spectra of dendrimers 10 and 11.

The EL spectra of the dendrimers 11 and 10 are shown in FIG. 13. The spectrum of 11 is slightly broader and exhibits less vibronic structure. The emission peaks at 518 nm, whereas the emission for 10 peaks at 532 nm and has a vibronic feature at 569 nm. There is a significant increase in the red tail emission of 11. The device consisting of 10 was more efficient than that containing 11.

EXAMPLE 17

Device results for G2-Pt-porphyrin (13)

Figure 14:
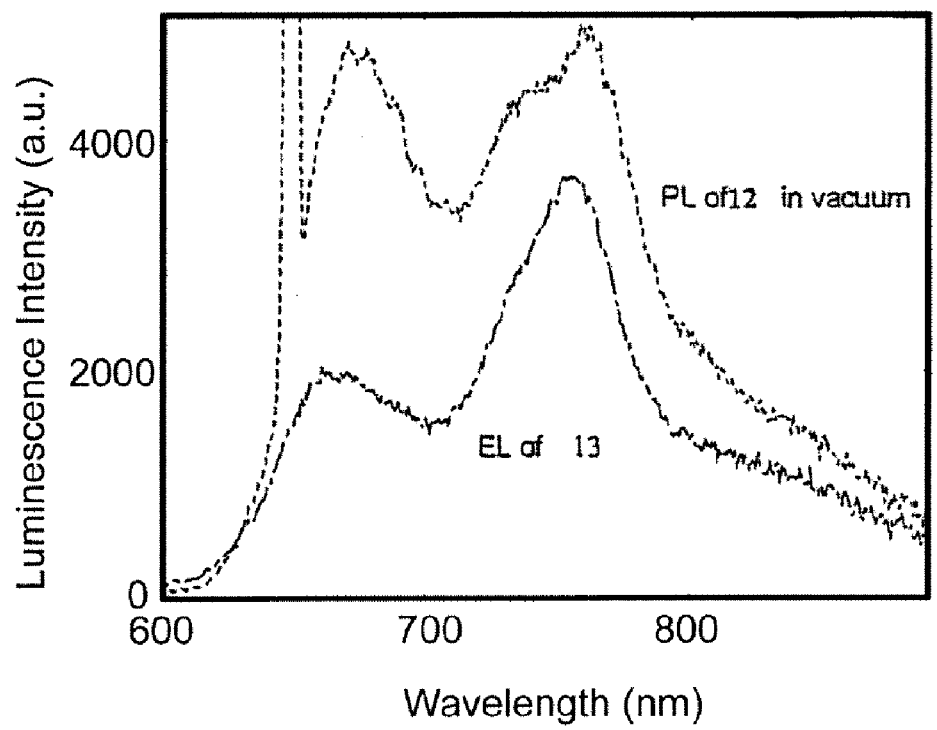
FIG. 14 shows the PL spectrum of 12 compared to the EL spectrum of dendrimer 13.

Single layer devices of neat G2-Pt-porphyrin dendrimer (13) were fabricated (PEDOT/13/Al). In FIG. 14, the EL spectrum of 13 is compared to the PL spectrum of the G1-Pt-porphyrin dendrimer (12). As has previously been observed in both free base and platinum porphyrin dendrimers, the EL spectra exhibit a stronger weighting of the lower energy emission peak.

EXAMPLE 18

Figure 15:
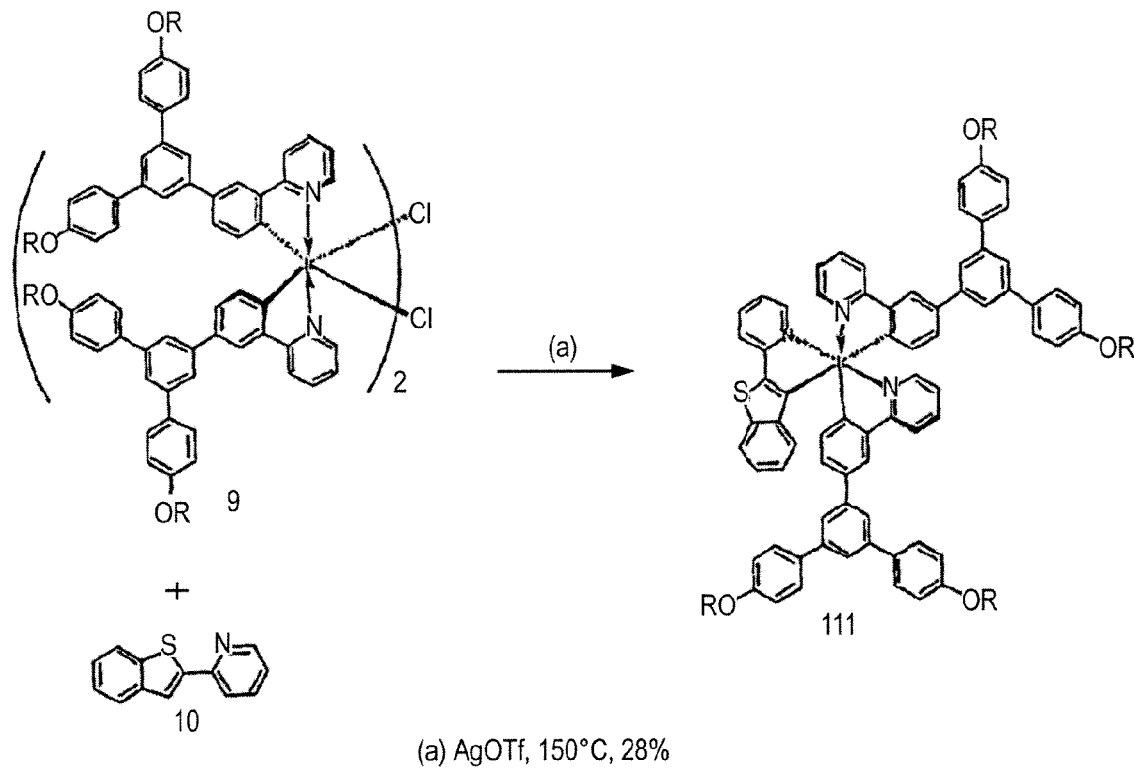
FIG. 15 shows a reaction scheme for the synthesis of the (G1ppy)$_2$ btpIr(III) dendrimer.

This example of a red emitting Ir dendrimer is illustrated in FIG. 15, and reference numbers apply accordingly.
(G1ppy)$_2$btpIr(III) (111)

Figure 16:
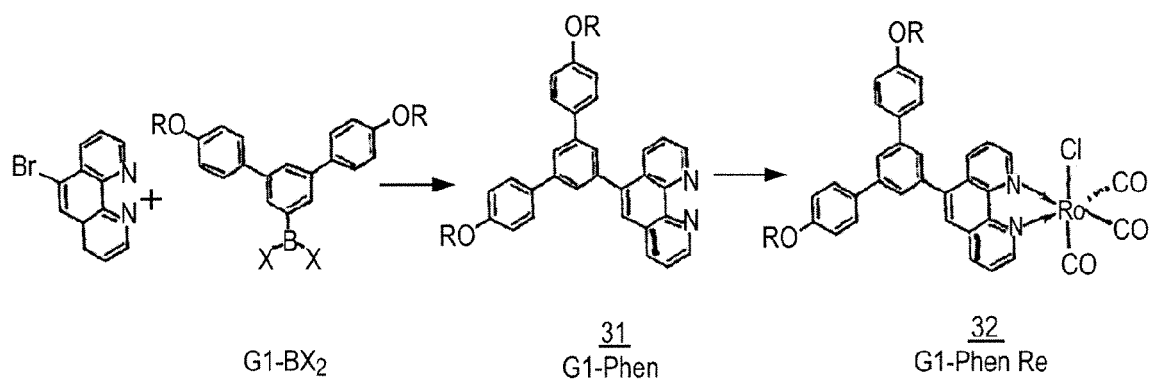
FIG. 16 shows a reaction scheme for the synthesis of tri-carbonyl-chloro-{3,5-[4'-(2''-ethylhexyloxy)phenyl]phenyl}phenanthroline rhenium.

Dichloromethane (5 mL) was added to a mixture of G1ppy Ir dimer (9) (411 mg, 0.317 mmol), 2-benzo[b]thiophen-2-ylpyridine (10) (1.44 g, 6.83 mmol) and silver trifluoromethanesulphonate (81 mg, 0.31 mmol) and the solution stirred at room temperature for 5 min and the solvent completely removed. The reaction is shown in FIG. 16. The mixture was then heated in the melt at 150° C. for 67.5 h and allowed to cool. The residue was purified by column chromatography over silica with dichloromethane-light petroleum (1:2 to 2:3) as eluent to give (G1ppy)$_2$btpIr(III)(111) (130.4 mg, 28%) as an orange solid. $\delta_H$(400 MHz, CDCl$_3$) 0.98 (24H, m, CH$_3$), 1.30-1.60 (32H, m, alkyl H), 1.79 (4H, m, OCH$_2$CH), 3.94 (8H, d, J 5.5, OCH$_2$) and 6.81-8.05 (41H, m, aromatic H). m/z (MALDI) 1681.4 (M$^+$, 100%).

A mixture of the above obtained iridium complex, recycled ligand 5 (about 244 mg), 2-(4'-G1-Ph)Py 5 (200 mg, 0.313 mmol) and silver trifluoromethanesulfonate (70 mg, 0.272 mmol) was heated (with bath temperature of 130-140° C.) for 88 h under argon. The reaction was then allowed to cool to room temperature and ~5 cm$^3$ of DCM was added. The brown yellow mixture was purified by column chromatography over silica gel with DCM-ethyl acetate-light petroleum (0:1:10 to 1:1:10) as eluent to give 200 mg (49% for two steps referring to IrCl$_3$.3H$_2$O) of 10 as an orange yellow solid; TGA$_{(5\%)}$ 410° C.; (Found: C, 76.8; H, 7.5; N, 2.0. C$_{135}$H$_{156}$IrN$_3$O$_6$ requires C, 76.9; H, 7.5; N, 2.0%); $_{max}$/nm (thin film) 277, and 397; $_H$(200 MHz; CDCl$_3$) 0.78-1.03 (36H, m, Me), 1.15-1.50 (48H, m, CH$_2$), 1.52-1.72 (6H, m, CH), 3.65 (12H, m, ArOCH$_2$), 6.58 (12H, m, ArH), 6.92 (3H, t, J 6.4 Hz, PyH), and 7.32-7.92 (39H, m, ArH & PyH); m/z [MALDI] 2105, 2106, 2107, 2108, 2109, 2110, 2111, 2112, 2113 (M$^+$).

EXAMPLE 19

Example 19 and 20, leading to the formation of a Re dendrimer, are illustrated in FIG. 16.

G1-Phen, 31

{3,5-[4'-(2"-Ethylhexyloxy)phenyl]phenyl}phenanthroline

Method 1 mixture of the Reference Example 6 compound G1-BX$_2$ (496 mg, 0.944 mmol), bromophenanthroline (221 mg, 0.858 mmol), 2 M Na$_2$CO$_{3(aq)}$ (0.5 cm$^3$), EtOH (0.5 cm$^3$) and toluene (1.5 cm$^3$ was degassed for 10 min under argon. Tetrakis(triphenylphosphine)palladium (0) (32 mg, 0.028 mmol) was added to the reaction mixture and then heated at reflux under argon for 22 h. The reaction was allowed to cool to room temperature and diluted with water (20 cm$^3$) and ether (20 cm$^3$). The two layers were separated. The aqueous layer was extracted with ether (3×20 cm$^3$). The organic layer and the ether extracts were combined and washed with water (1×40 cm$^3$), dried over anhydrous magnesium sulfate and the solvents were removed. Silica gel column chromatography using MeOH-ethyl acetate (1:0 to 1:10) gave 251 mg (40%) of 31 as a colourless oil; $v_{max}$/cm$^{-1}$ (KBr) 1607, 1590, and 1512; $\lambda_{max}$(CH$_2$Cl$_2$)/nm 269 ($\epsilon$/dm$^3$mol$^{-1}$cm$^{-1}$ 75850); $\delta_H$(200 MHz; CDCl$_3$) 0.89-0.99 (12H, m, Me), 1.26-1.59 (16H, m, CH$_2$), 1.71-1.80 (2H, m, CH), 3.90 (4H, m, ArOCH$_2$), 7.02 (4H, m, ArH), 7.57-7.70 (8H, m, ArH & PhenH), 7.85 (1H, s, PhenH), 7.87 (1H, t, J 1.6 Hz, ArH), 8.27 (1H, dd, J 8.1 & 1.7 Hz, PhenH), 8.43 (1H, dd, J 8.4 & 1.6 Hz, PhenH), 9.22 (1H, d, J 1.6 Hz, PhenH), 9.24 (1H, d, J 1.6 Hz, PhenH); $\delta_C$(50 MHz; CDCl$_3$) 11.1, 14.1, 23.0, 23.8, 29.1, 30.5, 39.4, 70.6, 114.9, 122.9, 123.4, 123.7, 124.8, 126.5, 128.2, 129.7, 32.8, 134.7, 136.0, 139.0, 139.7, 141.8, 146.4, 146.8, 150.1, 150.3, 150.7, 159.3; m/z [MALDI] 1393 (2M+Cu$^+$).

Method 2

A mixture of the first generation borolane (349 mg, 0.57 mmol), bromophenanthroline (221 mg, 0.855 mmole), 2 M Na$_2$CO$_{3(aq)}$ (4 cm$^3$), EtOH (4 cm$^3$) and toluene (16 cm$^3$) was degassed for 15 min under argon. Tetrakis(trisphenylphosphine)palladium (0) (21 mg, 0.018 mmol) was then added to the reaction mixture before being heated at reflux under argon for 22 h. The mixture was allowed to cool and diluted with water (20 cm$^3$) and ether (20 cm$^3$). The organic layer and the extracts were combined, washed with water (40 cm$^3$) and dried over anhydrous magnesium sulfate. The solvents were removed under vacuum. Purification on silica gel column using MeOH-ethyl acetate (0:1 to 1:9) as eluent gave 333 mg (88%) of 31 as a colourless oil.

EXAMPLE 20

G1-Phen Re, 32

Tricarbonyl-chloro-{3,5-[4'-(2"-ethylhexyloxy)phenyl]phenyl}phenanthroline rhenium A mixture of the phenanthroline ligand 31 (126 mg, 0.190 mmol) and pentacarbonylchloro rhenium (681 mg, 0.190 mmol) in 10 cm$^3$ of toluene was heated at reflux for 1.5 h. The mixture became yellow then orange. The reaction was allowed to cool to ambient temperature and the solvent was removed under reduce pressure. Purification on silica gel column using DM-light petroleum as eluent gave 76 mg (41%) of 32 as a bright yellow powder; $v_{max}$/cm$^{-1}$ (KBr) 2021, 1916, 1893; (Found: C, 60.5; H, 5.5; N, 2.8; C$_{49}$H$_{52}$ClN$_2$O$_5$Re requires C, 60.6; H, 5.4; N, 2.9%); $\lambda_{max}$/nm (thin film) 276; m/z [MALDI] 935 (M-Cl).

EXAMPLES 21-24

Figure 17:
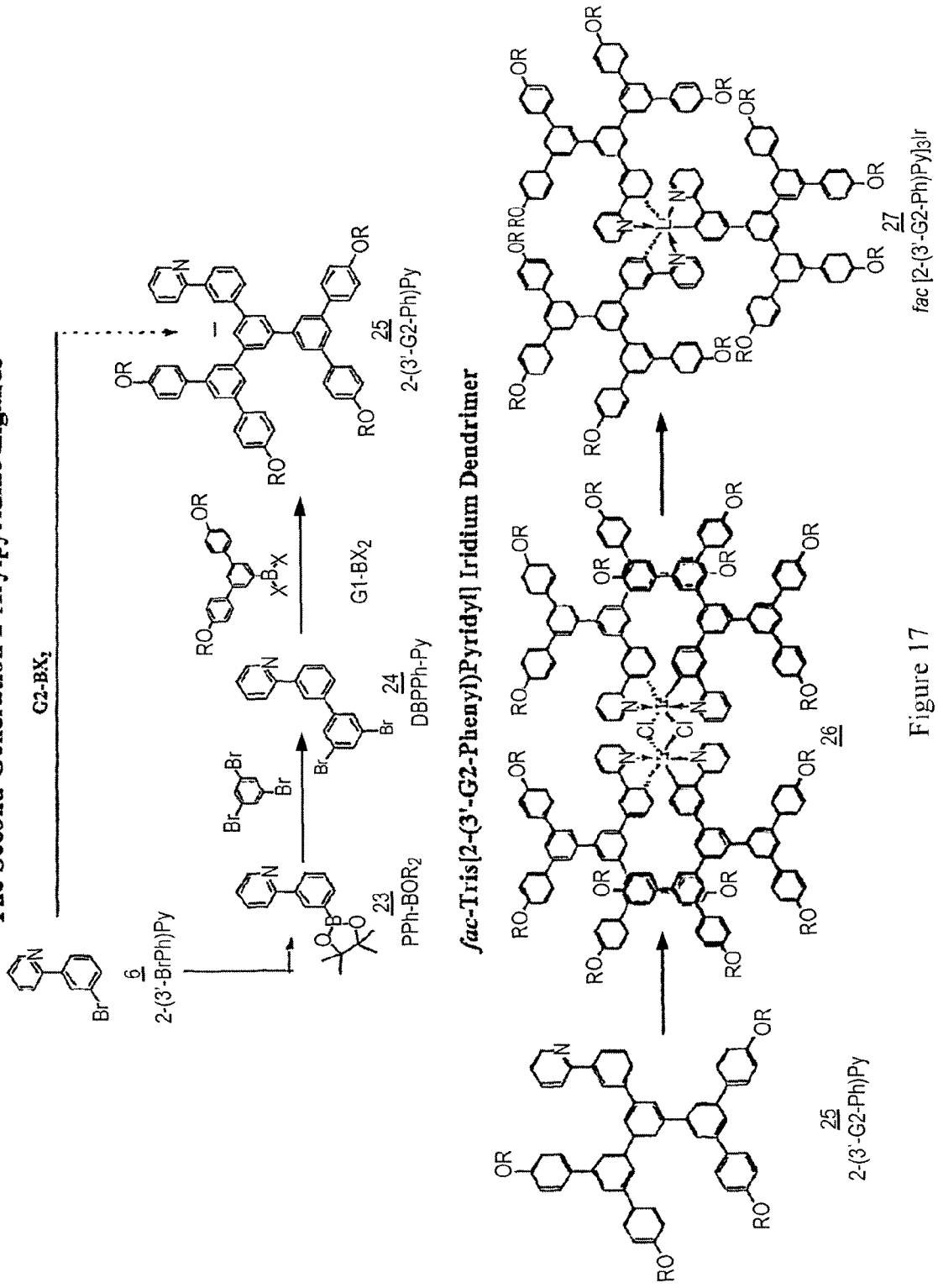
FIG. 17 shows a reaction scheme for the synthesis of the second generation 2-arylpyridine ligands.

These Examples are illustrated in FIG. 17

EXAMPLE 21

PPh-BOR$_2$

2-[3'(4",4",5",5"-tetramethyl-1",3",2"-dioxaborolan-2"-yl)phenyl]pyridine

Tert-butyl lithium (1.7 M, 36.6 cm$^3$, 62.1 mmol) was added to a cold (dry-ice/acetone bath) solution of 6 (8.10 g, 34.6 mmol) in 130 cm$^3$ of anhydrous THF under an argon atmosphere. The mixture was stirred at −78° C. for 2 h and then 2-isopropoxy-4,4,5,5-tetramethyl-1,3,2-dioxaborolane (9 cm$^3$) was added rapidly to the cold mixture. The reaction was stirred at −78° C. for 2 h and the dry-ice/acetone bath was removed. The mixture was then stirred at room temperature for further 20 h before being quenched with H$_2$O (30 cm$^3$). The two layers were separated. The aqueous layer was extracted with ether (3×40 cm$^3$)*. The organic layer and the ether extracts were combined and dried over anhydrous sodium sulfate and the solvents were completely removed.

*The aqueous layer was washed with NaHCO$_{3(sat)}$ (1×40 cm$^3$) and extracted with ether (2×40 cm$^3$) to give 4.0 g of yellow solid after being dried and removal of solvents. Purification of these crude mixture by column chromatography over silica gel using DCM-light petroleum (0:1 to 1:30) as eluent gave 4.92 g (50%) of 23 as a white solid; (Found: C, 72.6; H, 7.2; N, 5.0. C$_{17}$H$_{20}$BNO$_2$ requires C, 72.6; H, 7.2; N, 5.0%); $\delta_H$(400 MHz; CDCl$_3$) 1.37 (12H, s, Me), 7.23 (1H, m, PyH), 7.51 (1H, m, ArH), 7.76 (1H, m, PyH), 7.80 (1H, m, ArH), 7.87 (1H, m, PyH), 8.14 (1H, m, ArH), 8.40 (1H, and 8.71 (1H, m, PyH); $\delta_C$(101 MHz; CDCl$_3$) 24.9, 83.9, 120.7, 122.0, 128.2, 129.9, 133.2, 135.3, 136.6, 138.7, 149.6, 154.6, and 157.5; m/z [APCI$^+$] 283 (MH$^+$).

EXAMPLE 22

DBPPh-Py, 24

2-[3'-(3",5"-Di-bromophenyl)phenyl]pyridine

A mixture of 23 (5.15 g, 281 mmol), 1,3,5-tribromobenzene (6.92 g, 315 mmol), tetrakis(triphenylphosphine)palladium (0) (846 mg, 0.732 mmol), 2 M Na$_2$CO$_{3(aq)}$ (12 cm$^3$), EtOH (12 cm$^3$) and toluene (48 cm$^3$) was degassed and then heated at reflux (with bath temperature of 105-110° C.) under argon for 19.5 h. The mixture was allowed to cool. Water (10 cm$^3$) and ether (20 cm$^3$) were added to the mixture. The two phases were separated. The aqueous layer was extracted with ether (3×20 cm$^3$). The organic layer and the ether extracts were combined and dried over anhydrous sodium sulfate. The solvents were completely removed. The residue was purified by column chromatography over silica gel using ethyl acetate-light petroleum (0:1 to 1:20) as eluent to give 4.70 g (66%) of 24 as a white solid; (Found: C, 52.6; H, 2.5; N, 3.6. C$_{17}$H$_{11}$Br$_2$N requires C, 52.5; H, 2.9; N, 3.6%); $\delta_H$(400 MHz; CDCl$_3$) 7.29 (1H, m, PyH), 7.57 (2H, m, ArH), 7.67 (1H, m, ArH), 7.75 (2H, m, ArH), 7.79 (2H, m, PyH), 7.99 (1H, m, ArH), 8.19 (1H, m, ArH), and 8.74 (1H, m, PyH); $\delta_C$(101

MHz; CDCl$_3$) 120.7, 122.5, 123.2, 125.7, 126.9, 127.6, 129.1, 129.4, 132.7, 136.9, 138.9, 140.2, 144.6, 149.8, and 156.8; m/z [EI] 386, 388, 390 (MH$^+$).

EXAMPLE 23

2-(3'-G2-Ph)Py, 25

2-[3'-(3",5"-{3''',5'''-Di[4''''-(2'''''-ethylhexyloxy)phenyl]phenyl}phenyl)phenyl]pyridine A mixture of the boronic compound of Reference Example 6 (: G1-BX$_2$) (4.50 g, 8.48 mmol), 2-[3'-(3",5"-Di-bromophenyl)phenyl]pyridine (1.32 g, 3.39 mmol), tetrakis(triphenylphosphine)palladium (0) (274 mg, 0.237 mmol), 2 M Na$_2$CO$_{3(aq)}$ (3.7 cm$^3$), EtOH (3.7 cm$^3$) and toluene (10 cm$^3$) was degassed and then heated at reflux (with bath temperature of 110° C.) under argon for 69 h before being cooled. The mixture was diluted with water (4 cm$^3$) and ether (10 cm$^3$). The two layers were separated. The aqueous layer was extracted with ether (3×10 cm$^3$). The organic layer and the ether extracts were combined, washed with brine (1×30 cm$^3$), dried (Na$_2$SO$_4$) and the solvents were removed to leave a light yellow oil. The oil was purified by column chromatography over silica gel using ethyl acetate-light petroleum (0:1 to 1:30) and then DCM-light petroleum (1:20 to 1:10) as eluent to give 2.97 g (73%) of 25 as a white foam; (Found: C, 84.8; H, 8.7; N, 1.1. C$_{85}$H$_{101}$NO$_4$ requires C, 85.0; H, 8.5; N, 1.2%); λ$_{max}$/nm (thin film) 271; δ$_H$(400 MHz; CDCl$_3$) 0.90-1.02 (24H, m, Me), 1.33-1.60 (32H, m, CH$_2$), 1.73-1.88 (4H, m, CH), 3.94 (8H, m, ArOCH$_2$), 8.05 (8H, m, ArH), 7.23-7.32 (1H, m, PyH), 7.62-7.73 (9H, m, ArH), 7.77-7.90 (9H, m, PyH & ArH), 8.02 (3H, m, ArH), 8.07 (1H, m, ArH), 8.38 (1H, m, ArH), and 8.76 (1H, m, PyH); δ$_C$(101 MHz; CDCl$_3$) 11.1, 14.1, 23.1, 23.9, 29.1, 30.5, 39.4, 70.5, 114.9, 120.8, 122.3, 124.4, 124.7, 125.7, 126.1, 126.2, 128.0, 128.4, 129.4, 133.2, 136.8, 140.1, 141.6, 142.1, 142.2, 142.4, 142.7, 150.0, 157.3, and 159.2; m/z [MALDI] 1201, 1202, 1203, 1204, 1205 (MH$^+$).

EXAMPLE 24

Fac[2-(3'-G2-Ph)Py]$_3$Ir. 27

Fac tris{2-[3'-(3",5"-di{3''',5'''-di[4''''-(2'''''-ethylhexyloxy)phenyl]phenyl}phenyl)phenyl]pyridine}iridium (III)

A mixture of 25 (2.97 g, 2.47 mmol), iridium chloride tri-hydrate (174 mg, 0.50 mmol), H$_2$O (4 cm$^3$) and 2-ethoxyethanol (13 cm$^3$) was heated (bath temperature: 107° C.) under argon for 60 h before being cooled. The precipitate was filtered off* purified by a silica gel column using DCM-light petroleum (1:30 to 1:10) gave a yellow solid (900 mg) as the chloro-bridged dimer 26; δ$_H$(500 MHz; CDCl$_3$) 0.82-1.08 (96H, m, Me), 1.32-1.63 (128H, m, CH$_2$), 1.74-1.88 (16H, m, CH), 3.93 (32H, m, ArOCH$_2$), 6.26 (4H, m, ArH), 6.98 (4H, m, PyH), 7.06 (32H, m, ArH), 7.16 (4H, ArH), 7.71 (32H, m, ArH), 7.80-8.03 (44H, m, ArH & PyH), 8.18 (4H, m, PyH), and 9.51 (4H, m, PyH); δ$_C$(126 MHz; CDCl$_3$) 11.6, 14.6, 23.5, 24.3, 29.5, 31.0, 39.8, 71.0, 115.3, 119.4, 123.1, 124.7, 124.9, 125.5, 128.8, 131.6, 133.8, 134.9, 137.0, 142.5, 142.8, 143.0, 143.5, 145.0, 145.8, 152.2, 159.6, and 168.8; m/z [MALDI] 2591, 2592, 2593 (C$_{170}$H$_{200}$IrN$_2$O$_8$—CL$^+$), 2626 (C$_{170}$H$_{200}$IrN$_2$O$_8$).

*Meanwhile, the excess of 25 was recycled (1.96 g) from the solution after purified by column chromatography over silica gel using ethyl acetate-light petroleum (1:30 to 1:10) as eluent.

A mixture of the above obtained iridium complex (900 mg), the recycled 25 (1.96 g) and silver trifluoromethanesulfonate (300 mg) was heated (bath temperature: 145° C.) for a week under argon. The reaction was then allowed to cool to room temperature. The brown yellow mixture was dissolved in 50 cm$^3$ of DCM and then concentrated to about 10 cm$^3$ before being purified on silica gel column with eluent of DCM-light petroleum (1:20) as eluent to give >750 mg (>40% for two steps referring to IrCl$_3$.3H$_2$O) of 27 as a yellow solid; TGA$_{(5\%)}$ 400° C.; (Found: C, 80.7; H, 8.0; N, 1.1. C$_{255}$H$_{300}$IrN$_3$O$_2$ requires C, 80.8; H, 8.0; N, 1.1%); λ$_{max}$/nm (thin film) 271, 340 (sh), and 390; δ$_H$(400 MHz; CD$_2$Cl$_2$) 0.82-1.02 (72H, m, Me), 1.28-1.61 (96H, m, CH$_2$), 1.70-1.84 (12H, m, CH), 3.91 (24H, m, ArOCH$_2$), 6.97-7.12 (30H, ArH & PyH), 7.22 (3H, m, ArH), 7.43 (3H, m, PyH), 7.72 (24H, m, ArH), 7.78 (3H, m, PyH), 7.82 (6H, m, ArH), 7.93 (12H, m, ArH), 8.02 (3H, m, ArH), 8.09 (6H, m, ArH), and 8.14-8.24 (6H, m, PyH & ArH); m/z [MALDI] 3791 (broad) (M$^+$).

EXAMPLE 25

| Compound | Device structure | Peak efficiency (PE) (cd/A) | Voltage at PE | Brightness at PE (cd/m$^2$) | Max brightness and voltage cd/m$^2$ at V | Turn on voltage (V) |
|---|---|---|---|---|---|---|
| 111 G1-btpIrppy2 FIG. 15 | ITO/111 (50 nm)/Ca (20 nm)/Al (100 nm) | 0.15 | 13 | 850 | 938 at 13 | 4.0 |
| 111 G1-btpIrppy2 FIG. 15 | ITO/111:CBP (20:80 wt %) (110 nm)/Ca 20 nm)/Al (100 nm) | 3.0 | 14 | 1260 | 3836 at 18 | 6.0 |
| 111 G1-btpIrppy2 FIG. 15 | ITO/PEDOT (45 nm)/111:CBP (20:80 wt %) (110 nm)/Ca (20 nm)/Al (100 nm) | 3.7 | 14 | 390 | 2388 at 20 | 6.0 |
| 111 G1-btpIrppy2 FIG. 15 | ITO/111:TCTA (13:87 wt %) (45 nm/TPBI (45 nm)/LiF (0.6 nm)/Ca (20 nm)/Al (100 nm) | 3.2 | 6.8 | 60 | 3713 at 15 | 4.0 |
| 27 G2-Irppy3 FIG. 17 | ITO/27 (120 nm)/Ca (20 nm)/Al (100 nm) | 7.0 | 12 | 1250 | >6000 at 17 | 4.2 |
| 27† G2-Irppy3 FIG. 17 | ITO/27 (40 nm)/BCP (60 nm)/LiF (1.2 nm)/Al (100 nm) | 18 | 6.0 | 40 | >100 at 7.0 | 4.0 |

-continued

Figure 6:
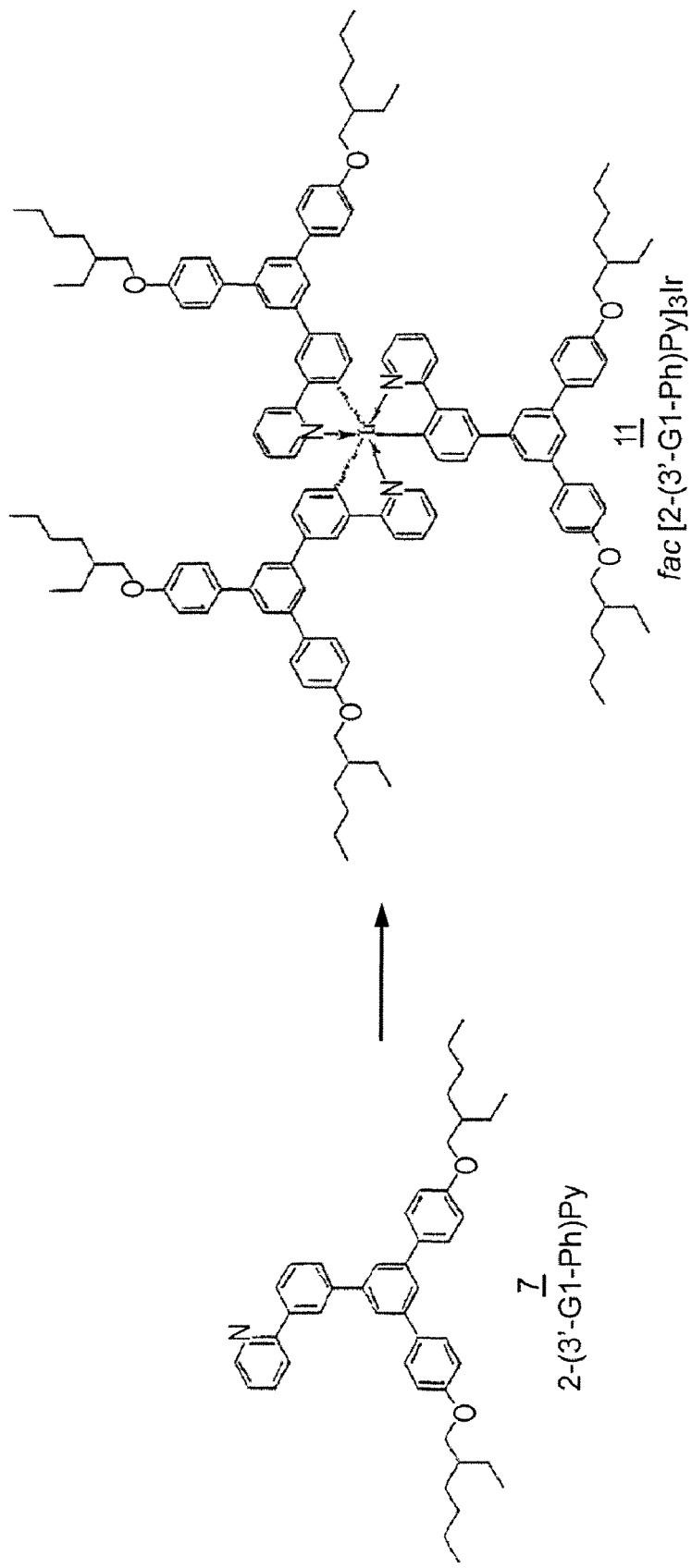
FIG. 6 shows the structure of Fac tris[2-(3'-G1-phenyl)pyridine]iridium (III) complex.
Figure 7:
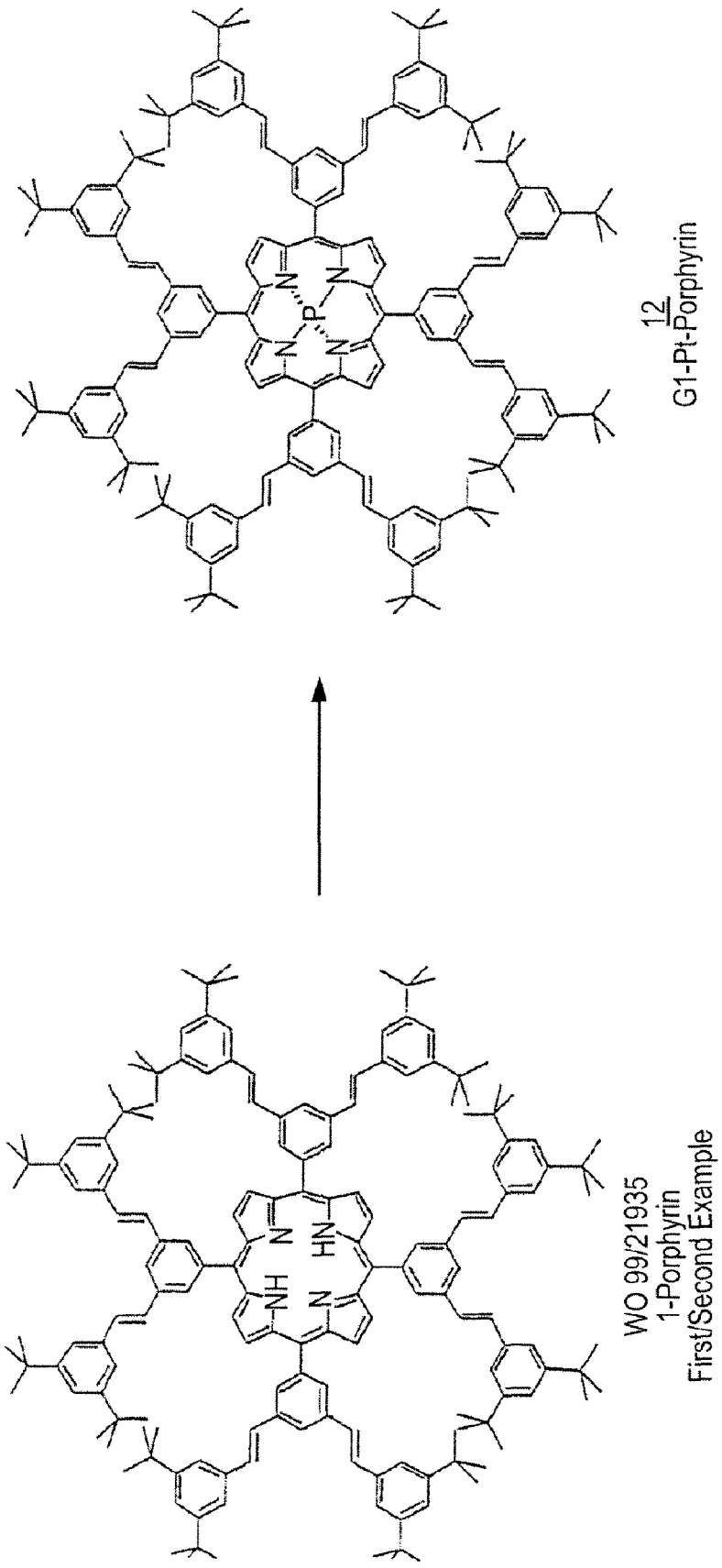
FIG. 7 shows the structure of Pt G1-porphyrin dendrimer.
Figure 8:
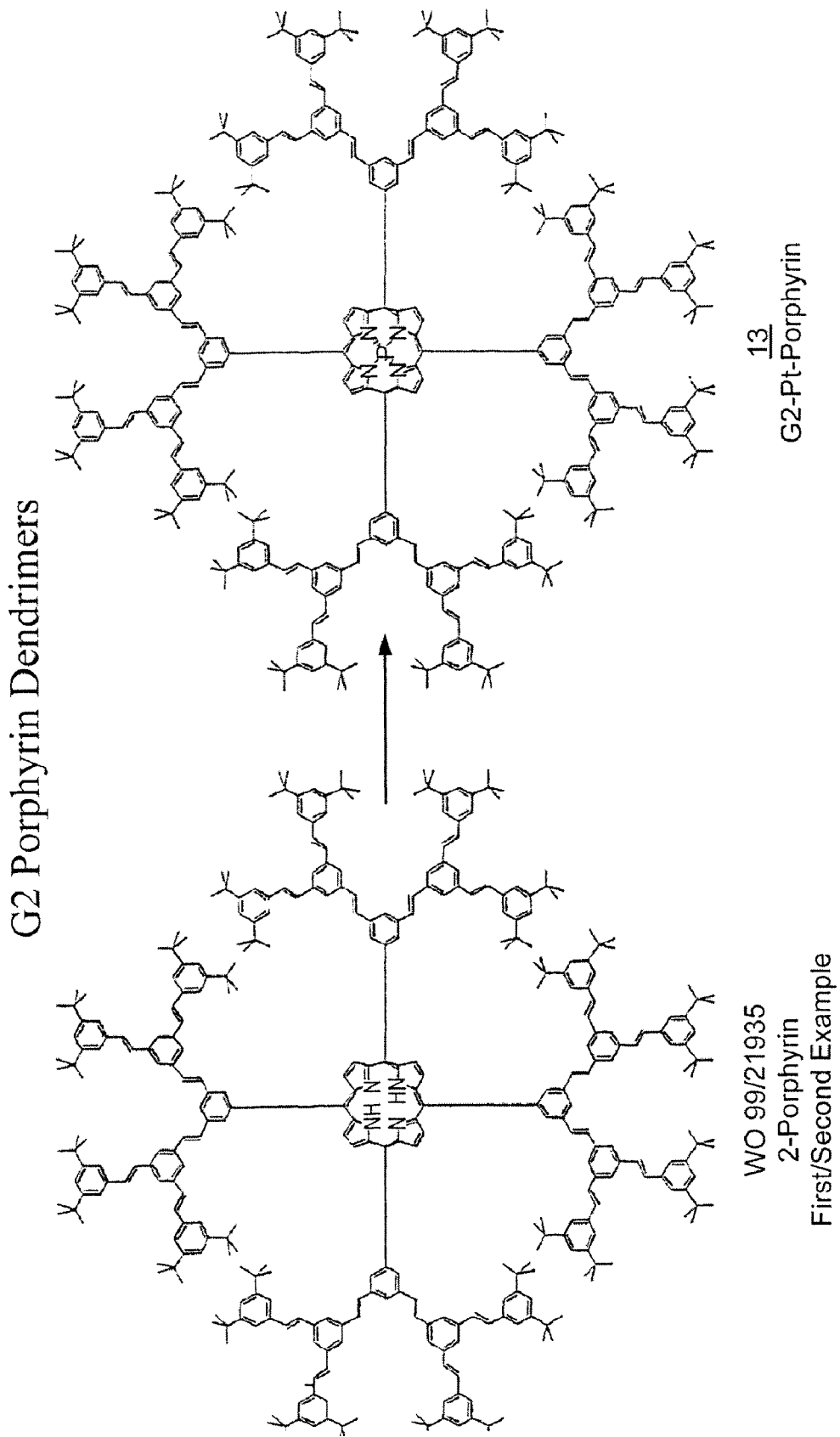
FIG. 8 shows the structure of Pt G2-porphyrin dendrimer.

| Compound | Device structure | Peak efficiency (PE) (cd/A) | Voltage at PE | Brightness at PE (cd/m$^2$) | Max brightness and voltage cd/m$^2$ at V | Turn on voltage (V) |
|---|---|---|---|---|---|---|
| 27† G2-Irppy3 FIG. 17 | ITO/27:TCTA (30:70 wt %)/TPBI (60 nm)/LiF (1.2 nm)/Al (100 nm) | 35-40 | 3.8 | 50-150 | 5066 at 6.0 | >3.0 |
| 27† G2-Irppy3 FIG. 17 | ITO/27:CBP (46:54 wt %)/BCP (60 nm)/LiF (1.2 nm)/Al (100 nm) | 23 | 6.0 | 30 | 1000 at 10 | 4.4 |
| 11 G1-Irppy3 FIG. 6 | ITO/11:TCTA (13:87 wt %)/BCP (60 nm)/LiF (1.2 nm)/Al (100 nm) | 30 | 5.0-6.0 | 100-250 | 3900 at 8.0 | 3.3 |
| 11 G1-Irppy3 FIG. 6 | ITO/11:TCTA (13:87 wt %)/TPBI (60 nm)/LiF (1.2 nm)/Al (100 nm) | 45-50 | 4.0 | 114 | 3005 at 6.0 | >3.0 |
| 32 G1-Re FIG. 16 | ITO/32:EHP-TCTA (25:75 wt %) (100 nm)/Ca (20 nm)/Al (100 nm) | 0.12 | 8.4 | 21 | 250 at 15 | 3.8 |
| 11 G1-Irppy3 | ITO/11:CBP (20:80 wt %)/Ca (20 nm)/Al (100 nm) | 28 | 13.4 | 3450 | | |
| 11 G1-Irppy3 | ITO/11:CBP (20:80 wt %) (120 nm)/LiF/Ca (20 nm)/Al (100 nm) | 37.5 | 12.2 | 2250 | 9970 | 3.6 |
| 11 G1-Irppy3 | ITO/11:CBP:TPBI (21:51; 28 wt %) (120 nm)/LiF/Ca (20 nm)/Al (100 nm) | 46 | 8.6 | 1000 | 9980 | 2.7 |

The results given above were obtained from devices which were prepared according to one of the following procedures.
Standard Device (no PEDOT)
1. Etch ITO squares 12×12 mm into 4×12 mm ITO strip by acid etch
2. Acetone rinse for 10 minutes with ultrasonication
3. Propan-2-ol rinse for 10 minutes with ultrasonication
4. Substrates dried under dry nitrogen flow
5. Substrates subject to oxygen plasma treatment for 5 minutes at 100 W
6. Dendrimer film deposited by spin coating
7. Substrates placed in vacuum evaporator
8. 20 nm of calcium deposited at 0.1 nm/s under vacuum of 1×10$^{-6}$ mBar
9. 100 nm of aluminium deposited at 0.1 nm/s under vacuum of 1×10$^{-6}$ mBar In step 6, typically a solution concentration of 20 mg/ml was used to achieve a film thickness of 100-120 nm, and a concentration of 5 mg/ml was used to achieve as film thickness of 45-50 nm. The solvent was usually ChCl$_3$ and the spin rate 2000 rpm for 60 sec.
For the devices with PEDOT the following steps were carried out between steps 5 and 6:
A. PEDOT spun from water solution at 2500 rpm for 1 minute
B. PEDOT layer dried in air at 85° C. for 5 minutes
    TCTA is tris(carbazolyl)triphenylamine
    EHP-TCTA was prepared as in Example Z.
    CBP is 4,4'-N,N'-dicarbazole-biphenyl.
    BCP is 2,9-dimethyl-4,7-diphenyl-1,10-phenanthroline.
    TPBI is 2,2',2"-(1,3,5-phenylene(tris[1-phenyl-1H-benzimidazole].
    Devices for 11† and 27† were prepared in the following manner. ITO substrates were patterned by photolithographic methods, cut into squares 1"×1" and cleaned sequentially in detergent, NH$_3$: H$_2$O$_2$, 1:1 and deionized water for 1 hour in an ultrasonic bath before drying in a stream of dry nitrogen. The dry substrates were transferred into a dry N$_2$ atmosphere glove-box where they were subjected to O$_2$ plasma treatment (Emitech K1050X plasma unit) at 60 W for 4 mins. Films of the dendrimer doped CBP or TCTA were deposited on the substrates by spin-coating inside the glove-box. Spin-coating was performed using solutions in CHCl$_3$ (CBP and TCTA) or toluene (TCTA) at a concentration of 5 mg/ml with spin rate 2000 rpm for 1 min. The dried spin-coated films were then transferred to the chamber of a vacuum evaporator without exposure to air for vacuum-deposition of subsequent organic charge transport layers and/or metal electrodes at low pressure (<10$^{-6}$ ton). The thickness of the evaporated layers was monitored by an in-situ quartz crystal microbalance and material was deposited at a rate of 0.1-0.5 nm/s.

Devices based on 11 and 27 emit green light with C.I.E. co-ordinates around (0.31, 0.63) whilst devices based on 111 emit red light with C.I.E. co-ordinates around (0.64, 0.35).

As can be seen from the results in the table, for the green emitting Ir dendrimers it can be advantageous to blend the dendrimer with a charge-transporting material (TCTA or CBP). A hole-blocking layer (TPBI) between the missive layer and the cathode can give a further efficiency improvement. It was found that the ratio of 11 to TCTA was fairly flexible, and over a range of 5-11 mol % there was little variation in the efficiency of the device. It can be advantageous to blend the phosphorescent dendrimer with both an electron-transporting material (TPBI) and a bipolar charge transport material (CBP) as this allows a remarkably high efficiency to be achieved from a device with only a single organic layer (final row in the Table).

EXAMPLE Z

Figure 18:
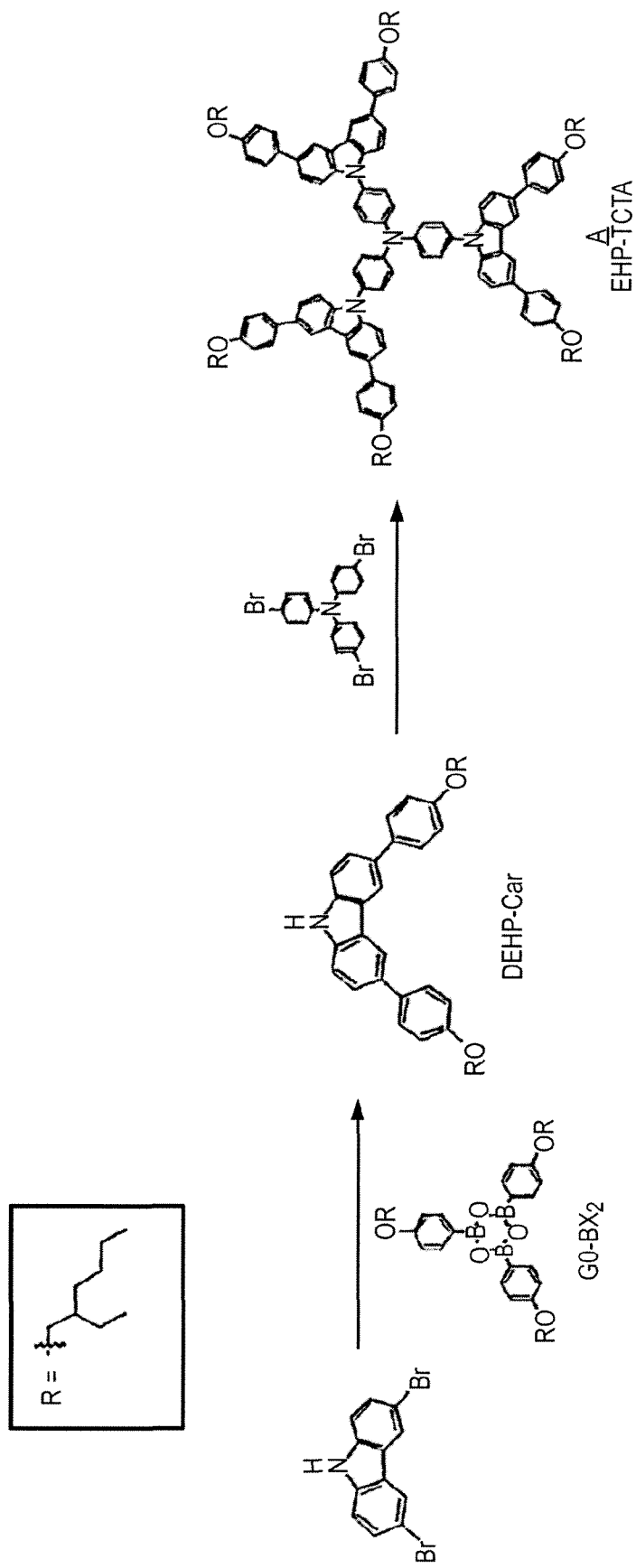
FIG. 18 shows a reaction scheme for the synthesis of tris (4-{3'',6''-di[4'''-(2''''-ethylhexyloxy)phenyl]carbaxolyl}phenyl)amine.

This example is illustrated in FIG. 18.

EHP-TCTA

Tris(4-{3",6"-DI[4"'-(2""-ethylhexyloxy)phenyl]carbazolyl}phenyl)amine

Tris(dibenzylideneacetone)di-palladium (0) [Pd$_2$(dba)$_3$] 14 mg, 0.015 mmol) and tri-tert-butylphosphine (10% in hexane, 0.01 cm$^3$) were added to a degassed (Schlenk line, evacuated and back-filled with argon) mixture of carbazolyl compound (3,6-di[4'-(2"-ethylhexyloxy)phenyl]carbazole; DEHP-Car) (860 mg, 1.49 mmol), tris(4-bromophenyl)amine (200 mg, 0.415 mmol), sodium tert-butoxide (240 mg, 2.49 mmol), and distilled toluene (1.0 cm$^3$) and xylenes (1.0 cm$^3$). The dark purple mixture was degassed again before being heated at reflux (with bath temperature of 130° C.) under argon for 4 days. The mixture was allowed to cool and quenched with $H_2O$ (0.5 cm$^3$) and purified by column chromatography over silica gel using DCM-light petroleum (0:1 to 1:10) as eluent to give 468 mg (57% of Z as a light brown yellow solid; TGA$_{(5\%)}$ 375° C.; $\lambda_{max}$/nm (thin film) 266, and 304; $\delta_H$(500 MHz; CDCl$_3$) 0.93-1.09 (36H, m, Me), 1.33-1.674 (8H, m, Ch$_2$), 1.78-1.89 (6H, m, CH), 3.95 (12H, m, ArOCH$_2$), 7.07 (12H, m, ArH), 7.54-7.77 (36H, m, ArH & CarH), and 8.40 (6H, m, CarH); $\delta_C$(126 MHz; CDCl$_3$) 11.6, 14.6, 23.6, 24.4, 29.6, 31.1, 39.9, 71.1, 110.6, 115.4, 118.9, 124.5, 125.8, 125.9, 128.5, 128.7, 133.4, 133.9, 134.7, 140.9, 146.8, and 159.1; m/z [MALDI] 1967, 1968, 1769, 1970, 1971 (MH$^+$).

DEHP-Car was prepared as follows:

A mixture of 3,6-dibromocarbazole (12.0 g, 37.1 mmol), the boronic compound G0-BX$_2$ (Reference Example 4) (24.1 g, 96.4 mmol), tetrakis(triphenylphosphine)palladium (0) (800 mg, 0.692 mmol), 2 M Na$_2$CO$_{3(aq)}$ (40 cm$^3$), EtOH (40 cm$^3$) and toluene (100 cm$^3$) was degassed and then heated at reflux (with bath temperature of 100° C.) under argon for 42 h. The mixture was allowed to cool and diluted with $H_2O$ (30 cm$^3$) and ether (40 cm$^3$). The two layers were separated. The aqueous layer was extracted with ether (3×40 cm$^3$). The organic layer and the ether extracts were combined, washed with brine (1×50 cm$^3$) and dried (Na$_2$SO$_4$). The solvents were completely removed and purified by column chromatography over silica gel using ethyl acetate-light petroleum (0:1 to 1:10) and DCM-ethyl acetate-light petroleum (4:1:20) as eluent to give 14.7 g (69%) of DEHP-Car as a white solid; m/z [APCI$^+$]576 (M$^+$).

EXAMPLE 26

Figure 19:
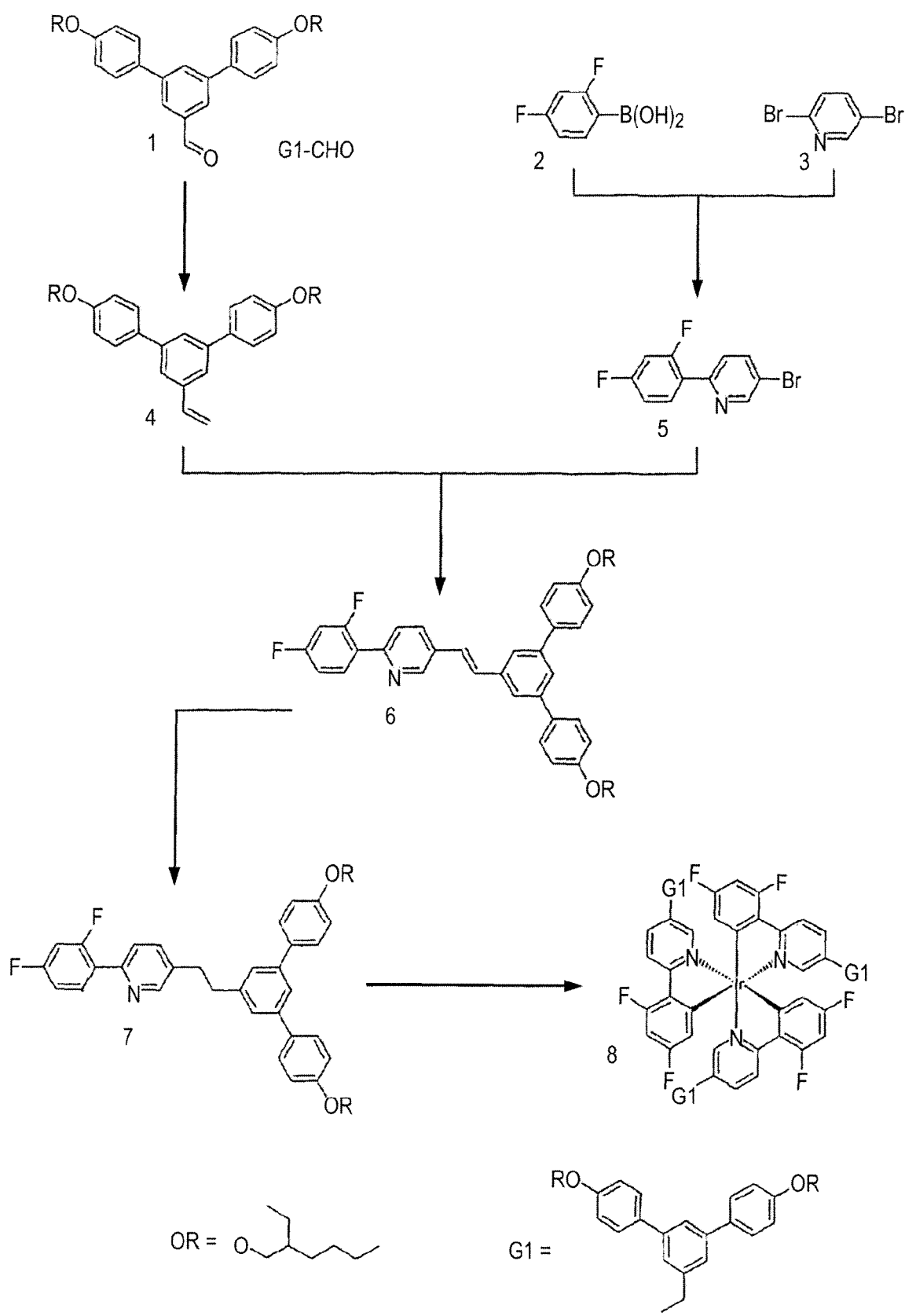
FIG. 19 shows an example (26) of a blue emitting Ir dendrimer.

This example of a blue emitting Ir dendrimer is illustrated in FIG. 19 and reference numbers apply accordingly.

G1-Styrene (4)

Potassium tert-butoxide (0.98 g, 8.76×10$^{-3}$ mol) was added slowly to a stirred mixture of compound (I) [Reference Example R3] (3.00 g, 5.84×10$^{-3}$ mol) and methyltriphenylphosphonium iodide (2.83 g, 7.01×10$^{-3}$ mol) in THF (30 cm$^3$). The mixture was stirred for 1.5 h at RT and the solvent removed in vacuo, petroleum fraction 60-80° C. (75 cm$^3$) was added, the mixture stirred for 10 min, passed through a pad of silica and the product eluted with petroleum fraction 60-80° C.-DCM 4:1 to yield a colourless oil.

Yield 2.0 g (67%); $\delta_H$(200 MHz; CDCl$_3$) 7.60 (m, 6H), 7.35 (s, 1H) 7.02 (d, 4H), 6.85 (dd, 10H), 5.88 (d, 1H), 5.35 (d, 1H), 3.92 (d, 4H), 1.78 (hept, 2H), 1.70-1.25 (m, 16H), 0.96 (m, 12H)

2-(2,4-difluorophenyl)-5-bromopyridine (5)

A mixture of 2,4-difluorophenylboronic acid (2) (0.37 g, 2.32×10$^{-3}$ mol), 2,5-dibromopyridine (3) (0.5 g, 2.11×10$^{-3}$ mol), tetrakis(triphenylphosphine)palladium (0) (80 mg, 6.96×10$^{-5}$ mol), aqueous sodium carbonate solution (2M, 0.2 cm$^3$), methanol (0.1 cm$^3$) and toluene (1.5 cm$^3$) was heated under reflux for 18 h. Water (10 cm$^3$) and DCM (15 cm$^3$) were added, the organic layer separated, dried over anhydrous magnesium sulphate, filtered and concentrated to a crystalline solid, which was purified by recrystallisation from ethanol twice.

Yield 240 mg (42%); $\delta_H$(500 MHz; CDCl$_3$) 8.81 (d, 1H), 8.06 (m, 1H), 7.93 (m, 1H), 7.72 (m, 1H), 7.07 (m, 1H), 6.98 (m, 1H)

Compound (6)

A mixture of compound (5) (306 mg, 1.13×10$^{-3}$ mol), compound (4) (696 mg, 1.36×10$^{-3}$ mol), Herrmann's catalyst (12 mg, 1.28×10$^{-5}$ mol), N,N-dimethylacetamide (6 cm$^3$), sodium carbonate (0.13 g) and 2,6-di-tert-butyl-p-cresol (0.14 g, 2.86×10$^{-4}$ mol) was heated at 140° C. for 2 d. DCM (10 cm$^3$) and water (10 cm$^3$) were added, the organic layer separated, washed with water (10 cm$^3$), dried over anhydrous magnesium sulphate, filtered and concentrated to a brown oil which was purified by column chromatography [silica gel, hexane eluting to DCM; repeated—silica gel, DCM] to yield a pale brown oil.

Yield 316 mg (40%) $\delta_H$(200 MHz; CDCl$_3$) 8.91 (d, 1H), 8.10 (, 2H), 7.86-6.95 (m, 16H), 3.92 (d, 4H), 1.78 (hept, 2H), 1.70-1.25 (m, 16H), 0.96 (m, 12H)

Compound (7)

A mixture of compound (6) (450 mg, 6.41×10$^{-4}$ mol) and palladium on carbon (5% w/w, 34 mg) in THF (7 cm$^3$) was stirred vigorously under an atmosphere of hydrogen for 18 h. The mixture was passed through a pad of celite and rinsed through with DCM (75 cm$^3$). The solution was concentrated to a pale brown oil which was purified by column chromatography [silica gel, DCM].

Yield 357 mg (79%); $\delta_H$(200 MHz; CDCl$_3$) 8.56 (d, 1H), 8.00 (m, 1H), 7.75-6.85 (m, 15H), 3.91 (d, 4H), 3.08 (s, 4H), 1.78 (hept, 2H), 1.70-1.25 (m, 16H), 0.96 (m, 12H)

Compound (8)

A mixture of compound (7) (175 mg, 2.49×10$^{-4}$ mol), iridium (III) chloride trihydrate (40 mg, 1.13×10$^{-4}$ mol), 2-butoxyethanol (2.2 cm$^3$) and water (0.35 cm$^3$) was heated at 140° C. for 20 h. DCM (10 cm$^3$) and w ater (10 cm$^3$) were added, the organic layer separated and concentrated to a yellow oil which was purified by column chromatography [silica gel, DCM-petroleum fraction 60-80° C. 1:1] to yield a yellow oil. Compound (7) (65 mg, 9.29×10$^{-5}$ mol) and silver triflate (25 mg, 9.88×10$^{-5}$ mol) were added and the mixture heated at 140° C. for 24 h. The product was purified by column chromatography [silica gel, DCM petroleum fraction 60-80° C. 1:1 repeated 3 times] to yield a yellow glassy solid.

Yield 11 mg (5%) $\delta_H$(400 MHz; CDCl$_3$) 8.16 (d, 3H), 7.62-6.82 (m, 42H), 6.30 (m, 6H), 3.86 (m, 12H), 2.70 (m, 12H), 1.73 (hept, 6H), 1.70-1.25 (m, 48H), 0.96 (m, 36H)

The PL data for this dendrimer are as follows:

A thin film of a blend of compound 8 and CBP (20 wt % of compound 8) was prepared by spin coating the dendrimer/CBP mixture from a long/ml solution in DCM at 2000 rpm for 1 min. The CIE co-ordinates of the PL emission (excitation at 333 nm) were x=0.144, y=0.326.

It should be noted that in this example, as in the other Ir dendrimer examples, all three of the groups coordinating to the Ir are covalently bound via Ir—C and Ir—N bonds. Such covalently bound systems may have advantages in to/ns of stability over systems in which one of the three coordinating groups is more ionic in character.

The invention claimed is:

1. A light emitting device which comprises at least one layer that contains an organometallic dendrimer with a metal cation as part of its core, said core not comprising a magnesium chelated porphyrin, wherein the organometallic dendrimer is blended with at least one other dendrimer and/or polymer and/or molecular material.

2. A device according to claim 1, further comprising a light emitting layer, wherein the organometallic dendrimer is in the light emitting layer.

3. A device according to claim 2, further comprising at least one charge transporting and/or injecting layer.

4. A device according to claim 1, wherein the organometallic dendrimer is a light emitting material.

5. A device according to claim 1, wherein the organometallic dendrimer is provided as a homogeneous layer.

6. A device according to claim 1, wherein the organometallic dendrimer is fluorescent in the solid state.

7. A device according to claim 1, wherein the organometallic dendrimer is phosphorescent in the solid state.

8. A device according to claim 1, wherein the organometallic dendrimer has at least one inherently at least partially conjugated dendron.

9. A device according to claim 8, wherein the HOMO-LUMO energy gap of the core is lower than that of the conjugated moieties in the dendrons.

10. A device according to claim 8, wherein the HOMO-LUMO energy gap of the moieties in the dendrons decreases from the surface to the point of attachment to the core.

11. A device according to claim 8, wherein the organometallic dendrimer has at least two inherently at least partially conjugated dendrons.

12. A device according to claim 11, wherein all the dendrons are inherently at least partially conjugated.

13. A device according to claim 1, wherein the organometallic dendrimer is phosphorescent in the solid state and is blended with a corresponding non-metallic dendrimer which possesses the same dendritic structure as that of the organometallic dendrimer.

14. A device according to claim 1, wherein the molar ratio of organometallic dendrimer to other dendrimer and/or polymer and/or molecular material is from 1:1 to 1:100.

15. A device according to claim 1, wherein the organometallic dendrimer has the formula (I):

CORE-[DENDRITE]$_n$,  (I)

in which CORE represents a metal ion or a group containing a metal ion, n represents an integer of 1 or more, each DENDRITE, which may be the same or different, represents an inherently at least partially conjugated dendritic molecular structure comprising aryl groups and/or (hetero)aryl groups or nitrogen and, optionally, vinyl or acetylenyl groups connected via sp$^2$ or sp hybridized carbon atoms of said (hetero)aryl, vinyl and acetylenyl groups or via single bonds between nitrogen and said (hetero)aryl groups, said CORE terminating in the single bond which is connected to an sp$^2$ hybridized (ring) carbon atom of the first (hetero)aryl group or nitrogen to which more than one at least partially conjugated dendritic branch is attached, said ring carbon atom or nitrogen forming part of said DENDRITE.

16. A device according to claim 15, wherein DENDRITE does not include nitrogen as a branching point and is an inherently at least partially conjugated dendritic molecular structure.

17. A device according to claim 1, wherein the organometallic dendrimer has the formula (II):

CORE-[DENDRITE$^1$]$_n$[DENDRITE$^2$]$_m$  (II)

in which CORE represents a metal ion or a group containing a metal ion, n and m, which may be the same or different, each represent an integer of at least 1, each DENDRITE$^1$, which may be the same or different when n is greater than 1, and each DENDRITE$^2$, which may be the same or different when m is greater than 1, both represent dendritic structures including at least one branching point, and optionally at least one link between branching points, at least one of said structures being conjugated and comprising aryl groups and/or (hetero)aryl groups or nitrogen and, optionally, vinyl and/or acetylenyl groups, connected via sp$^2$ or sp hybridized carbon atoms of said (hetero)aryl, vinyl and acetylenyl groups or via single bonds between nitrogen and said (hetero)aryl groups, the branching points and/or the links between the branching points in DENDRITE$^1$ being different from those in DENDRITE$^2$, said CORE terminating in the single bond which is connected to a sp$^2$ hybridized (ring) carbon atom of the first (hetero)aryl group or nitrogen to which more than one conjugated dendritic branch is attached, said ring carbon atom or nitrogen forming part of said conjugated DENDRITE$^1$ or DENDRITE$^2$ and CORE terminating at the single bond to the first branching point for the other of said DENDRITE$^1$ or DENDRITE$^2$, and at least one of the CORE, DENDRITE$^1$ and DENDRITE$^2$ being luminescent.

18. A device according to claim 1, wherein the organometallic dendrimer has the formula (III):

CORE-[DENDRITE]$_n$  (III)

in which CORE represents a metal ion or a group containing a metal ion, n represents an integer greater than 1, each DENDRITE, which may be the same or different, represents an inherently at least partially conjugated dendritic molecular structure which comprises aryl and/or heteroaryl or nitrogen and, optionally, vinyl and/or acetylenyl groups connected via sp$^2$ or sp hybridized carbon atoms of said (hetero)aryl, vinyl and acetylenyl groups or via single bonds between nitrogen and (hetero)aryl groups, each dendritic structure includes branching points, and links between adjacent branching points, and wherein the links between adjacent branching points are not all the same, said CORE terminating in the single bond which is connected to a sp$^2$ hybridized (ring) carbon atom of the first (hetero)aryl group or nitrogen to which more than one dendritic branch is attached, said ring carbon atom or nitrogen forming part of said DENDRITE, and at least one of the CORE and DENDRITE being luminescent.

19. A device according to claim 1, wherein the organometallic dendrimer comprises at least one coordinating group which is not dendritic.

20. A device according to claim 1, wherein the metal as part of the core is not magnesium.

21. A device according to claim 1, wherein the metal cation is a cation of a d-block metal.

22. A device according to claim 21, wherein the metal is iridium or rhenium.

23. A device according to claim 1, wherein the core comprises a metal ion and one of a porphyrin, a carboxylate, and a phenyl pyridine.

24. A device according to claim 1, wherein the metal ions are exclusively at the core.

25. A device according to claim 1, wherein said organometallic dendrimer has at least one dendron and at least one surface group attached to the distal end of the dendron.

26. A device according to claim 25, wherein the surface group is selected from the group consisting of a further-reactable alkene; (meth)acrylate; a sulphur-containing group; a silicon containing group; a polyether group; a C$_1$-to-C$_{15}$ alkyl group; an amine group; a —COOR group wherein R is hydrogen or C$_1$-to-C$_{15}$ alkyl; and an —OR group wherein R is hydrogen, aryl, C$_1$-to-C$_{15}$ alkyl or C$_1$-to-C$_{15}$ alkenyl.

27. A device according to claim 26, wherein the layer containing the organometallic dendrimer is deposited by solution processing.

28. A device according to claim 26, wherein the surface group is selected such as to allow solution processing.

29. A device according to claim 26, wherein the surface group is selected such as to allow the dendrimer to be photo patterned.

30. A device according to claim 1, wherein the device is a light emitting diode (LED).

31. A blend comprising an organometallic dendrimer which comprises a metal cation as part of its core and two or more dendrons, wherein at least one of said dendrons is conjugated and wherein the dendrimer is luminescent in the solid state, wherein the core does not comprise a magnesium chelated porphyrin, and wherein said organometallic dendrimer is blended with at least one other dendrimer and/or polymer and/or molecular material.

32. A blend according to claim 31 wherein the core is a complex of a metal cation and two or more coordinating groups, and at least two of the coordinating groups are bound to one of the dendrons.

33. The blend according to claim 31 wherein the organometallic dendrimer is phosphorescent in the solid state.

34. The blend according to claim 31, wherein the metal as part of the core is not magnesium.

35. The blend according to claim 31, wherein the metal ions are exclusively at the core.

36. The blend according to claim 31, wherein the organometallic dendrimer is blended with a corresponding non-metallic dendrimer having the same dendritic structure as that of the organometallic dendrimer.

37. The blend according to claim 36 wherein the molar ratio of organometallic dendrimer to non-organometallic dendrimer is from 1:1 to 1:100.

38. A process for producing a dendrimer blend as defined in claim 31, comprising:
(a) providing a core by forming a complex between a metal cation and two or more coordinating groups, at least two of the coordinating groups bearing a reactive functionality; and
(b) treating the core thus provided with two or more dendrons which have been functionalized to render them reactive towards the reactive functionalities present in the core, at least one of the dendrons being conjugated, thereby forming the organometallic dendrimer.

39. The process according to claim 38, wherein at least one of the coordinating groups does not contain a reactive functionality and consequently remains free of attachment to a dendron in step (b).

40. The process according to claim 38, wherein the core provided in step (a) is represented by formula (IV):

$$M[X\!-\!]_q Y_r \qquad (IV)$$

wherein M is a metal ion,
each [X—], which are the same or different, includes a reactive functionality and is a coordinating group X having a number (a) of coordination sites and being attached to a single bond in which CORE terminates,
each Y, which may be the same or different, is a coordinating group having a number (b) of coordination sites,
q is an integer,
r is 0 or an integer, and
the sum of [(a) multiplied by (q)]+[(b) multiplied by (r)] is equal to the number of coordination sites available on M.

41. A process for producing a dendrimer blend as defined in claim 31, comprising:

(a) attaching a coordinating group to each of two or more dendrons, and
(b) forming a complex between the coordinating groups and a metal cation which is optionally bonded to one or more ligands which remain in the resulting complex, thereby forming the organometallic dendrimer.

42. The process according to claim 41 wherein the complex formed between the coordinating groups and the metal cation in step (b) is represented by formula (IV):

$$M[X\!-\!]_q Y_r \qquad (IV)$$

wherein M is a metal ion,
each [X—], which are the same or different, is a coordinating group X having a number (a) of coordination sites and being attached to a single bond in which CORE terminates,
each Y, which may be the same or different, is a coordinating group having a number (b) of coordination sites,
q is an integer,
r is 0 or an integer, and
the sum of [(a) multiplied by (q)]+[(b) multiplied by (r)] is equal to the number of coordination sites available on M.

43. A process for producing a dendrimer blend as defined in claim 31, comprising:
(a) attaching a coordinating group to each of two or more dendrons;
(b) forming a complex between the coordinating groups and a metal cation; and
(c) optionally further treating said complex with one or more additional coordinating ligands, thereby forming the organometallic dendrimer.

44. A blend comprising an organometallic dendrimer of the formula $$\text{CORE-[DENDRITE]}_n, \qquad (I)$$

in which CORE represents a metal ion or a group containing a metal ion,
n represents an integer of 1 or more,
each DENDRITE, which may be the same or different, represents an inherently at least partially conjugated dendritic molecular structure comprising aryl groups and/or heteroaryl groups or nitrogen and, optionally, vinyl or acetylenyl groups connected via $sp^2$ or sp hybridized carbon atoms of said (hetero)aryl, vinyl and acetylenyl groups or via single bonds between nitrogen and said (hetero)aryl groups,
said CORE terminating in the single bond which is connected to an $sp^2$ hybridized (ring) carbon atom of the first (hetero)aryl group or nitrogen to which more than one at least partially conjugated dendritic branch is attached, said ring carbon atom or nitrogen forming part of said DENDRITE,
said CORE not comprising a magnesium chelated porphyrin, wherein
said organometallic dendrimer is blended with at least one other dendrimer and/or polymer and/or molecular material.

45. A blend comprising an organometallic dendrimer of the formula (II):

$$\text{CORE-[DENDRITE}^1]_n[\text{DENDRITE}^2]_m \qquad (II)$$

in which CORE represents a metal ion or a group containing a metal ion,
n and m, which may be the same or different, each represent an integer of at least 1,
each DENDRITE$^1$, which may be the same or different when n is greater than 1, and each DENDRITE$^2$, which may be the same or different when m is greater than 1, both represent dendritic structures including at least one branching point, and optionally at least one link between branching points, at least one of said structures being conjugated and comprising aryl groups and/or heteroaryl groups or nitrogen and, optionally, vinyl and/or acetylenyl groups, connected via $sp^2$ or sp hybridized carbon atoms of said (hetero)aryl, vinyl and acetylenyl groups or via single bonds between nitrogen and said (hetero)aryl groups, the branching points and/or the links between the branching points in $DENDRITE^1$ being different from those in $DENDRITE^2$, said CORE terminating in the single bond which is connected to a $sp^2$ hybridized (ring) carbon atom of the first (hetero)aryl group or nitrogen to which more than one conjugated dendritic branch is attached, said ring carbon atom or nitrogen forming part of said conjugated $DENDRITE^1$ or $DENDRITE^2$ and CORE terminating at the single bond to the first branching point for the other of said $DENDRITE^1$ or $DENDRITE^2$, and at least one of the CORE, $DENDRITE^1$ and $DENDRITE^2$ being luminescent, wherein said organometallic dendrimer is blended with at least one other dendrimer and/or polymer and/or molecular material.

46. The blend according to claim 44 wherein the CORE is represented by formula (IV):

$$M[X-]_q Y_r \qquad \text{(IV)}$$

wherein M is a metal ion, each [X—], which are the same or different, is a coordinating group X having a number (a) of coordination sites and being attached to a single bond in which CORE terminates, each Y, which may be the same or different, is a coordinating group having a number (b) of coordination sites, q is an integer, r is 0 or an integer, and the sum of [(a) multiplied by (q)]+[(b) multiplied by (r)] is equal to the number of coordination sites available on M.

* * * * *

UNITED STATES PATENT AND TRADEMARK OFFICE
CERTIFICATE OF CORRECTION

| | |
|---|---|
| PATENT NO. | : 7,906,902 B2 |
| APPLICATION NO. | : 12/564908 |
| DATED | : March 15, 2011 |
| INVENTOR(S) | : Paul L. Burn et al. |

It is certified that error appears in the above-identified patent and that said Letters Patent is hereby corrected as shown below:

In the Specification:

At Column 6, line 28, "metals as" should be -- metal as --.
At Column 30, line 28, "w ater" should be -- water --.

In the Claims:

At Column 31, line 67, "(hetero)aryl" should be -- heteroaryl --.

Signed and Sealed this
Fourteenth Day of February, 2012

David J. Kappos
*Director of the United States Patent and Trademark Office*